US011339190B2

(12) United States Patent
Pahan

(10) Patent No.: US 11,339,190 B2
(45) Date of Patent: May 24, 2022

(54) PEPTIDES FOR THE TREATMENT OF COVID-19

(71) Applicant: Rush University Medical Center, Chicago, IL (US)

(72) Inventor: Kalipada Pahan, Skokie, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 17/133,035

(22) Filed: Dec. 23, 2020

(65) Prior Publication Data

US 2021/0324004 A1 Oct. 21, 2021

Related U.S. Application Data

(60) Provisional application No. 63/078,547, filed on Sep. 15, 2020, provisional application No. 62/704,091, filed on Apr. 21, 2020.

(51) Int. Cl.
| | | |
|---|---|---|
| *C07K 7/06* | (2006.01) | |
| *C07K 7/08* | (2006.01) | |
| *A61K 9/00* | (2006.01) | |
| *A61P 31/14* | (2006.01) | |
| *A61K 38/10* | (2006.01) | |
| *A61K 38/08* | (2019.01) | |
| *A61K 38/00* | (2006.01) | |

(52) U.S. Cl.
CPC .............. *C07K 7/06* (2013.01); *A61K 9/0043* (2013.01); *A61K 38/08* (2013.01); *A61K 38/10* (2013.01); *A61P 31/14* (2018.01); *C07K 7/08* (2013.01); *A61K 38/00* (2013.01)

(58) Field of Classification Search
CPC .......... C07K 7/00; A61K 38/00; A61K 38/03; A61K 38/04; A61K 38/08; A61K 38/10
See application file for complete search history.

(56) References Cited

U.S. PATENT DOCUMENTS

| 10,214,592 B2 * | 2/2019 | Kikuchi ................ C12N 15/02 |
| 2007/0116716 A1 | 5/2007 | Shen et al. |
| 2018/0133327 A1 | 5/2018 | Derouazi |
| 2018/0258148 A1 | 9/2018 | Bames |

FOREIGN PATENT DOCUMENTS

| CN | 110951756 A | 4/2022 |
| WO | 2010047826 A2 | 4/2010 |

OTHER PUBLICATIONS

Hu et al. "Characteristics of SARS-CoV-2 and COVID-19", Nature Reviews Microbiology, EPUB Oct. 6, 2020, 141-154 (Year: 2020).*
Shang et al., Cell entry mechanisms of SARS-CoV-2, May 6, 2020, PNAS, 11727-11734. (Year: 2020).*
Lackie, "Prophylaxis", A Dictionary of Biomedicine (1 ed.), 2010 (Year: 2010).*
"Prophylaxis", Concise Medical Dictionary (9 ed.), 2015 (Year: 2015).*
Prophylaxis. (2015). In the Editors of the American Heritage Dictionaries (Ed.), The AmericanHeritage Dictionary of Medicine (2nd ed.). Houghton Miffl in. Credo Reference:https://search.credoreference.com/content/entry/hmmedicaldict/prophylaxis/0?institutionld=743 (Year: 2015).*
Machhi, Jatin, et al., "The Natural History, Pathobiology, and Clinical Manifestations of SARS-CoV-2 Infections", Journal of Neuroimmune Pharmacology, Jul. 1, 2020, (28 pp).
Whitlock, RN, MSN, FN, Jennifer, et al., "Types of Prophylaxis in Medicine", www.verywellhealth.com, Jan. 31, 2020, (7 pp).
United States Patent & Trademark Office, The International Search Report and The Written Opinion issued in corresponding International application No. PCT/US2021/028369, dated Mar. 21, 2022, 14 pp.
Ho et al., "Design and biological activities of novel inhibitory peptides for SARS-CoV spike protein and angiotensin-converting enzyme 2 interaction" Antiviral Research, Nov. 28, 2005 (Nov. 28, 2005), vol. 69, No. 2006, pp. 70-76, entire document.
Paidi, et al., "ACE-2 interacting Domain of SARS-CoV2 (AIDS_Peptide Suppresses Inflammation to Reduce Fever and Protect Lungs and Heart in Mice: Implications for COVID-19 Therapy," Journal of Neuroimmune Pharmacology, Jan. 11, 2021 (Jan. 11, 2021), vol. 16, No. 1, pp. 59-70, entire document.
Zhang, et al. "The first-in-class peptide binder to the SARS-CoV2 spike protein"; Mar. 20, 2020 [Retreived on Nov. 22, 2021] Retrieved from the internert: <URL:https://www.birxiv.org/content/10.1101/2020.03.19.999318v1.full.pdf>; pp. 1-15, entire document.

* cited by examiner

*Primary Examiner* — Lianko G Garyu
(74) *Attorney, Agent, or Firm* — Taft Stettinius & Hollister LLP; Joseph M. Bennett-Paris

(57) ABSTRACT

Compositions for inhibiting the binding between ACE2 and SARS-CoV-2 spike S1 are disclosed. Methods of treating COVID-19 are disclosed. Methods of making an in vivo model of COVID-19 are also disclosed.

19 Claims, 13 Drawing Sheets

Specification includes a Sequence Listing.

FIG. 1A

ACE2 — SARS-CoV-2 spike S1

FIG. 1B
AIDS peptides wtAIDS: $^{500}$TNGVGY$^{505}$
mAIDS: $^{500}$TGGVGD$^{505}$

FIG. 1C

ACE2 : S1 binding (% of control)

| Spike S1 | + | + | + | + | + | + |
| wtAIDS (μM) | 0 | 0.1 | 0.5 | 1.0 | 0 | 0 |
| mAIDS (μM) | 0 | 0 | 0 | 0 | 0.5 | 1.0 |

FIG. 1D

Rel. IL-6 mRNA; $p < 0.001$; NS NS

FIG. 1E

Rel. IL-1β mRNA; $p < 0.001$

| Spike S1 (ng/ml) | 0 | 1 | 1 | 1 | 1 | 1 |
| wtAIDS (μM) | 0 | 0 | 2 | 5 | 0 | 0 |
| mAIDS (μM) | 0 | 0 | 0 | 0 | 2 | 5 |

Rel. IL-6 mRNA / Rel. IL-1β mRNA; $p < 0.001$

| Poly IC (μg/ml) | 0 | 50 | 50 | 50 | 50 | 50 |
| wtAIDS (μM) | 0 | 0 | 2 | 5 | 2 | 5 |
| mAIDS (μM) | 0 | 0 | 0 | 0 | 2 | 5 |

Rel. IL-6 mRNA / Rel. IL-1β mRNA; $p < 0.001$

| Tat (150 ng/ml) | − | + | + | + | + | + |
| wtAIDS (μM) | 0 | 0 | 2 | 5 | 2 | 5 |
| mAIDS (μM) | 0 | 0 | 0 | 0 | 2 | 5 |

Rel. IL-6 mRNA / Rel. IL-1β mRNA; $p < 0.001$

| Flagellin (1 μM) | − | + | + | + | + | + |
| wtAIDS (μM) | 0 | 0 | 2 | 5 | 2 | 5 |
| mAIDS (μM) | 0 | 0 | 0 | 0 | 2 | 5 |

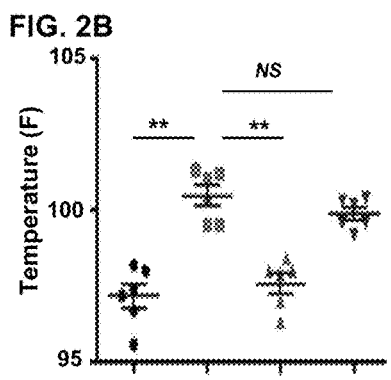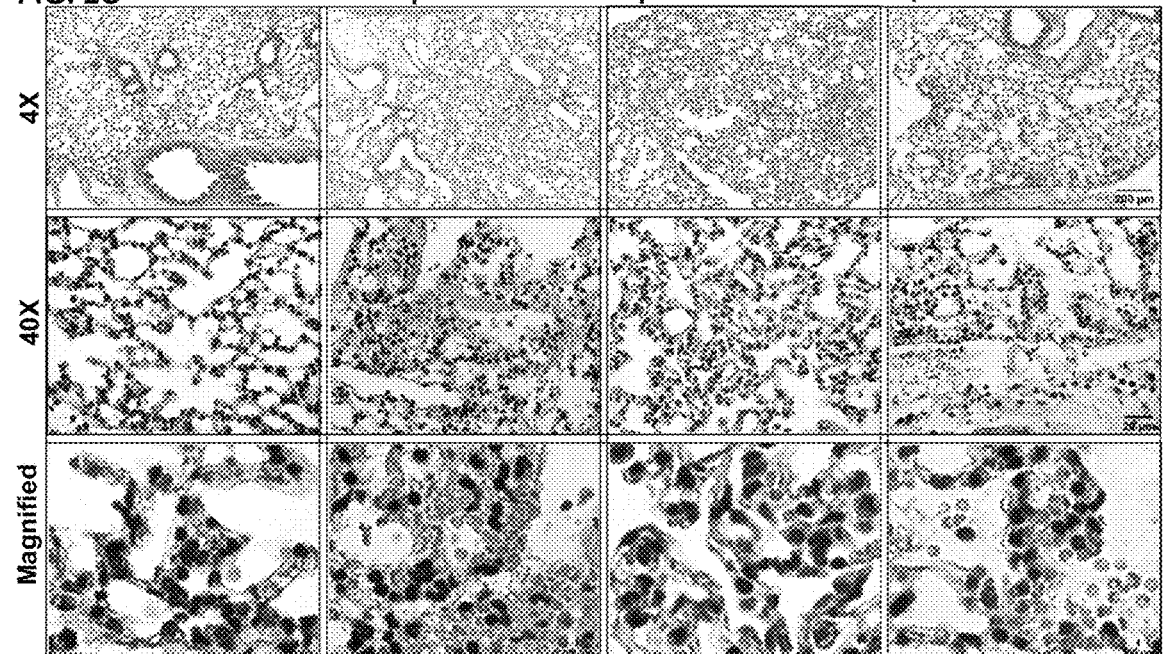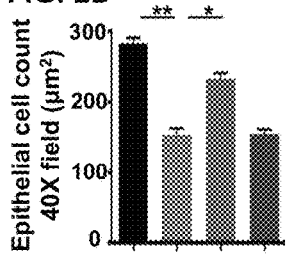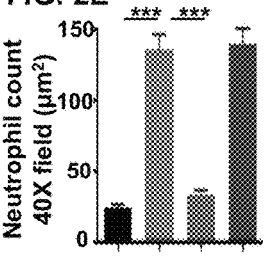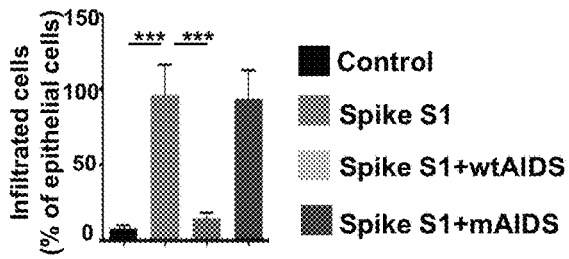

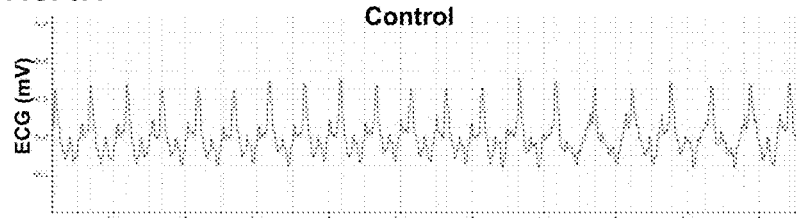
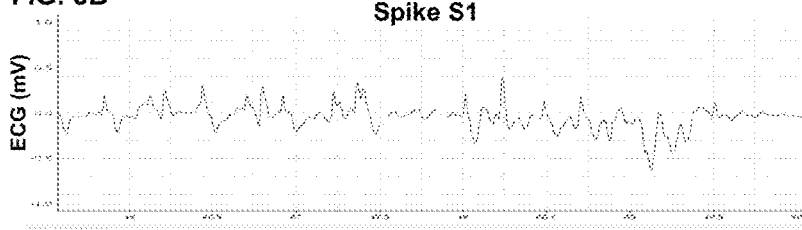
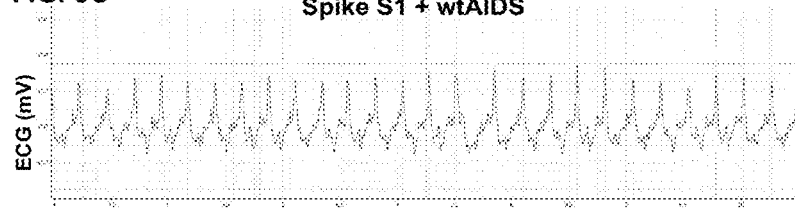
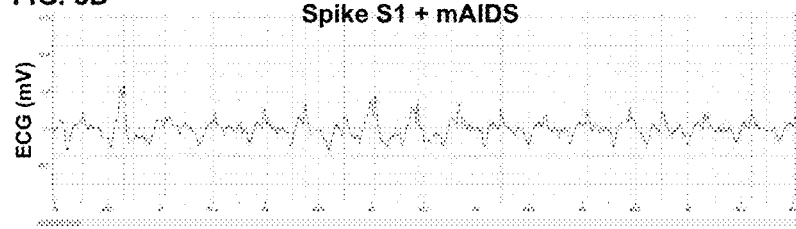
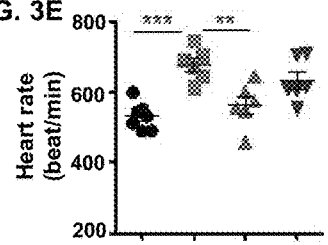
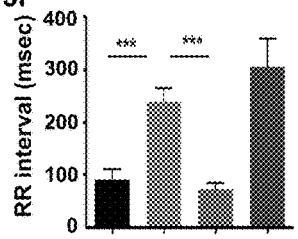
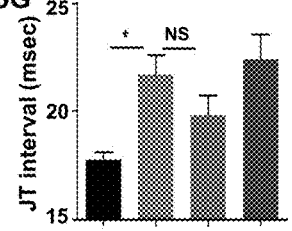
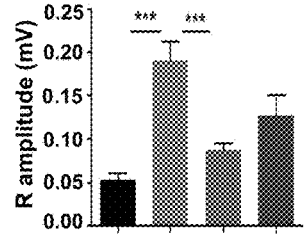
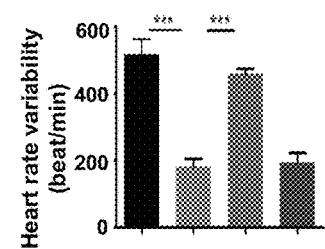
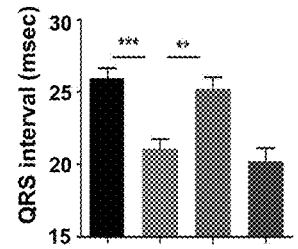
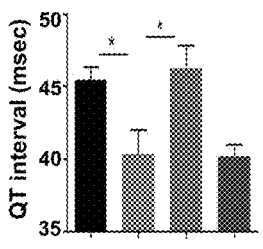

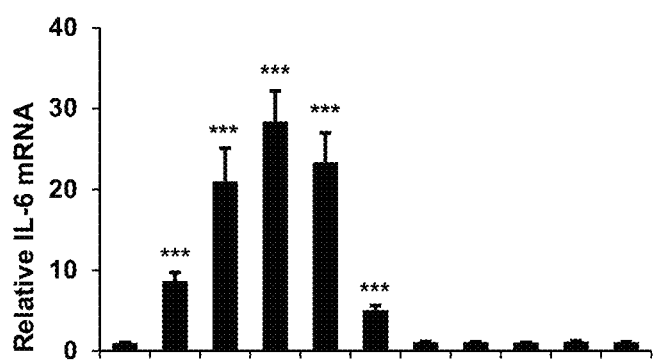
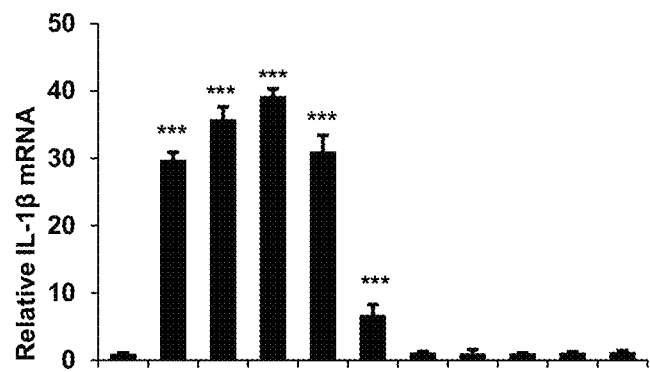

FIG. 8A  Control    Spike S1    Spike S1 + wtAIDS    Spike S1 + mAIDS
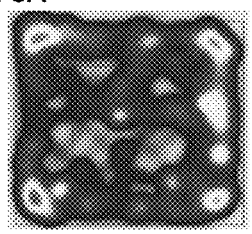 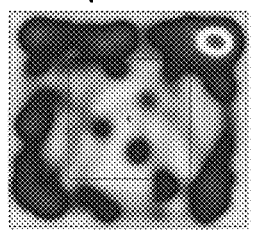 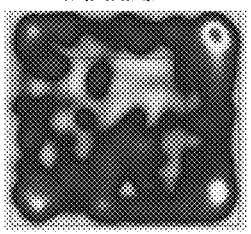 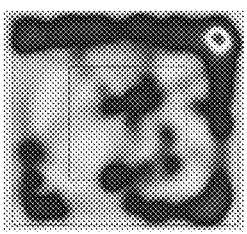
Fig. 8B 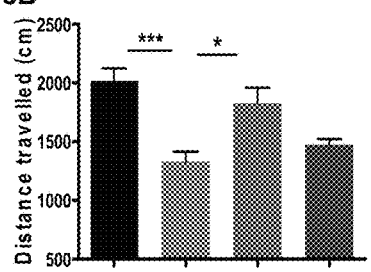  FIG. 8C 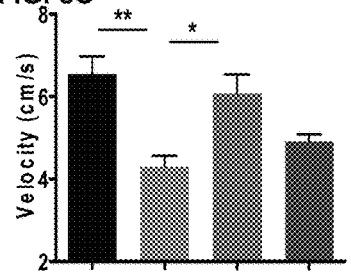  FIG. 8D 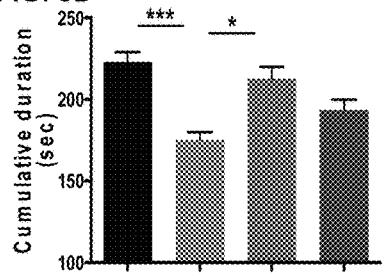

FIG. 9A    ACE2                          SARS-CoV-2 spike S1

Glu37
Asp38
Leu39
Phe40
Tyr41
Gln42

FIG. 9B
SPIDAR peptides wtSPIDAR: $^{37}$EDLFYQ$^{42}$ mSPIDAR: $^{37}$EKLFYG$^{42}$

FIG. 9C

ACE2 : S1 binding (% of control)

| Spike S1 | + | + | + | + | + | + |
| wtSPIDAR (µM) | 0 | 0.1 | 0.5 | 1.0 | 0 | 0 |
| mSPIDAR (µM) | 0 | 0 | 0 | 0 | 0.5 | 1.0 |

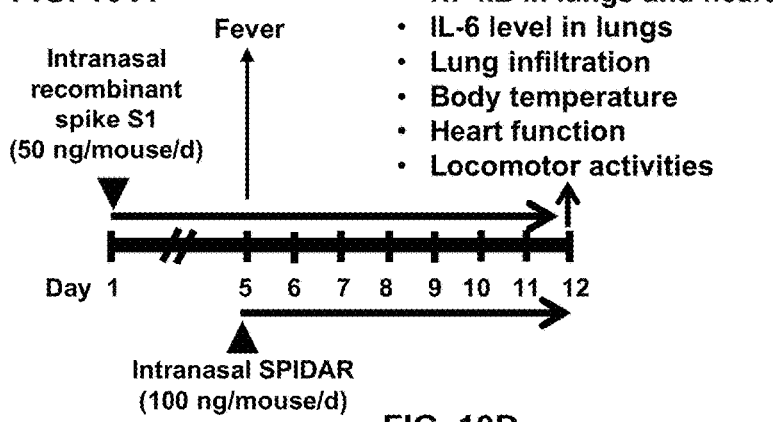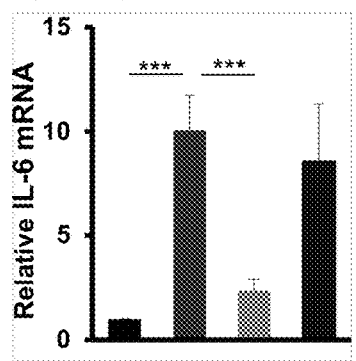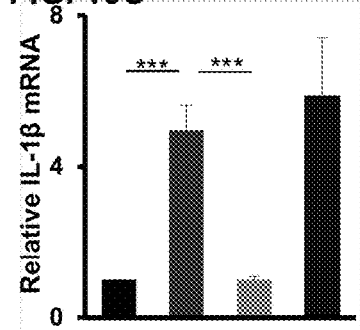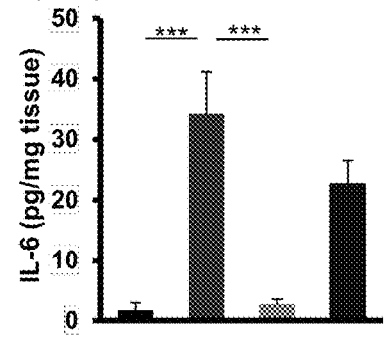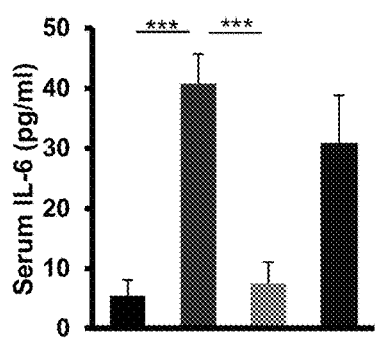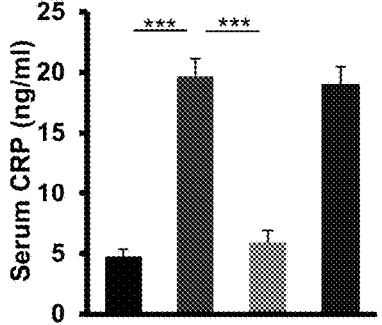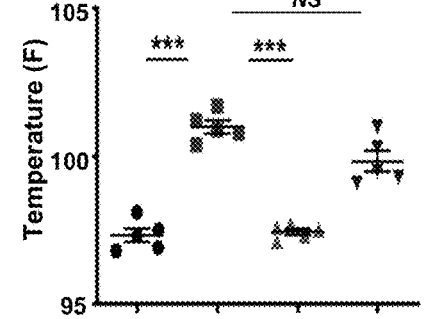

■ Control
■ Spike S1
■ Spike S1 + wtSPIDAR
■ Spike S1 + mSPIDAR

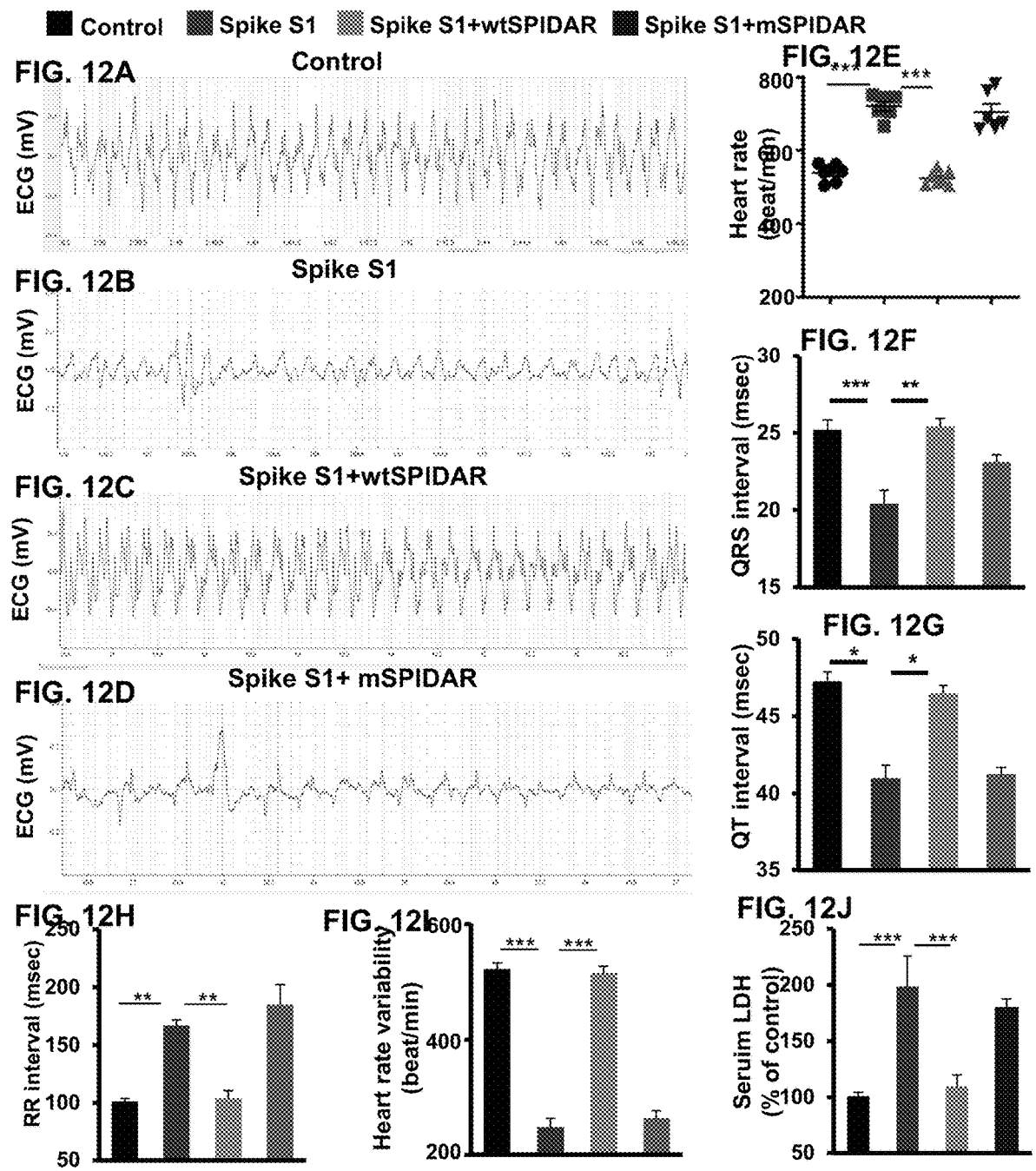

■ Control
■ Spike S1
■ Spike S1 + wtSPIDAR
■ Spike S1 + mSPIDAR

SEQUENCE LISTING

```
<160> NUMBER OF SEQ ID NOS: 15

<210> SEQ ID NO 1
<211> LENGTH: 672
<212> TYPE: PRT
<213> ORGANISM: Coronavirus

<400> SEQUENCE: 1

Ser Leu Val Ser Leu Leu Ser Val Leu Leu Met Gly Cys Val Ala Glu
1               5                   10                  15

Thr Gly Thr Gln Cys Val Asn Leu Thr Thr Arg Thr Gln Leu Pro Pro
            20                  25                  30

Ala Tyr Thr Asn Ser Phe Thr Arg Gly Val Tyr Tyr Pro Asp Lys Val
            35                  40                  45

Phe Arg Ser Ser Val Leu His Ser Thr Gln Asp Leu Phe Leu Pro Phe
50                  55                  60

Phe Ser Asn Val Thr Trp Phe His Ala Ile His Val Ser Gly Thr Asn
65                  70                  75                  80

Gly Thr Lys Arg Phe Asp Asn Pro Val Leu Pro Phe Asn Asp Gly Val
                85                  90                  95

Tyr Phe Ala Ser Thr Glu Lys Ser Asn Ile Ile Arg Gly Trp Ile Phe
            100                 105                 110

Gly Thr Thr Leu Asp Ser Lys Thr Gln Ser Leu Leu Ile Val Asn Asn
            115                 120                 125

Ala Thr Asn Val Val Ile Lys Val Cys Glu Phe Gln Phe Cys Asn Asp
        130                 135                 140

Pro Phe Leu Gly Val Tyr Tyr His Lys Asn Asn Lys Ser Trp Met Glu
145                 150                 155                 160

Ser Glu Phe Arg Val Tyr Ser Ser Ala Asn Asn Cys Thr Phe Glu Tyr
                165                 170                 175

Val Ser Gln Pro Phe Leu Met Asp Leu Glu Gly Lys Gln Gly Asn Phe
            180                 185                 190

Lys Asn Leu Arg Glu Phe Val Phe Lys Asn Ile Asp Gly Tyr Phe Lys
            195                 200                 205

Ile Tyr Ser Lys His Thr Pro Ile Asn Leu Val Arg Asp Leu Pro Gln
        210                 215                 220

Gly Phe Ser Ala Leu Glu Pro Leu Val Asp Leu Pro Ile Gly Ile Asn
225                 230                 235                 240

Ile Thr Arg Phe Gln Thr Leu Leu Ala Leu His Arg Ser Tyr Leu Thr
                245                 250                 255

Pro Gly Asp Ser Ser Ser Gly Trp Thr Ala Gly Ala Ala Ala Tyr Tyr
            260                 265                 270

Val Gly Tyr Leu Gln Pro Arg Thr Phe Leu Leu Lys Tyr Asn Glu Asn
            275                 280                 285

Gly Thr Ile Thr Asp Ala Val Asp Cys Ala Leu Asp Pro Leu Ser Glu
        290                 295                 300

Thr Lys Cys Thr Leu Lys Ser Phe Thr Val Glu Lys Gly Ile Tyr Gln
305                 310                 315                 320

Thr Ser Asn Phe Arg Val Gln Pro Thr Glu Ser Ile Val Arg Phe Pro
                325                 330                 335
```

```
Asn Ile Thr Asn Leu Cys Pro Phe Gly Glu Val Phe Asn Ala Thr Arg
            340                 345                 350

Phe Ala Ser Val Tyr Ala Trp Asn Arg Lys Arg Ile Ser Asn Cys Val
            355                 360                 365

Ala Asp Tyr Ser Val Leu Tyr Asn Ser Ala Ser Phe Ser Thr Phe Lys
370                 375                 380

Cys Tyr Gly Val Ser Pro Thr Lys Leu Asn Asp Leu Cys Phe Thr Asn
385                 390                 395                 400

Val Tyr Ala Asp Ser Phe Val Ile Arg Gly Asp Glu Val Arg Gln Ile
                405                 410                 415

Ala Pro Gly Gln Thr Gly Lys Ile Ala Asp Tyr Asn Tyr Lys Leu Pro
            420                 425                 430

Asp Asp Phe Thr Gly Cys Val Ile Ala Trp Asn Ser Asn Asn Leu Asp
            435                 440                 445

Ser Lys Val Gly Gly Asn Tyr Asn Tyr Leu Tyr Arg Leu Phe Arg Lys
        450                 455                 460

Ser Asn Leu Lys Pro Phe Glu Arg Asp Ile Ser Thr Glu Ile Tyr Gln
465                 470                 475                 480

Ala Gly Ser Thr Pro Cys Asn Gly Val Glu Gly Phe Asn Cys Tyr Phe
                485                 490                 495

Pro Leu Gln Ser Tyr Gly Phe Gln Pro Thr Asn Gly Val Gly Tyr Gln
            500                 505                 510

Pro Tyr Arg Val Val Val Leu Ser Phe Glu Leu Leu His Ala Pro Ala
            515                 520                 525

Thr Val Cys Gly Pro Lys Lys Ser Thr Asn Leu Val Lys Asn Lys Cys
            530                 535                 540

Val Asn Phe Asn Phe Asn Gly Leu Thr Gly Thr Gly Val Leu Thr Glu
545                 550                 555                 560

Ser Asn Lys Lys Phe Leu Pro Phe Gln Gln Phe Gly Arg Asp Ile Ala
                565                 570                 575

Asp Thr Thr Asp Ala Val Arg Asp Pro Gln Thr Leu Glu Ile Leu Asp
            580                 585                 590

Ile Thr Pro Cys Ser Phe Gly Gly Val Ser Val Ile Thr Pro Gly Thr
            595                 600                 605

Asn Thr Ser Asn Gln Val Ala Val Leu Tyr Gln Asp Val Asn Cys Thr
610                 615                 620

Glu Val Pro Val Ala Ile His Ala Asp Gln Leu Thr Pro Thr Trp Arg
625                 630                 635                 640

Val Tyr Ser Thr Gly Ser Asn Val Phe Gln Thr Arg Ala Gly Cys Leu
                645                 650                 655

Ile Gly Ala Glu His Val Asn Asn Ser Tyr Glu Cys Asp Ile Pro Ile
            660                 665                 670

<210> SEQ ID NO 2
<211> LENGTH: 805
<212> TYPE: PRT
<213> ORGANISM: Homo sapiens

<400> SEQUENCE: 2

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
```

```
                35                  40                  45
Asn Tyr Asn Thr Asn Ile Thr Glu Glu Asn Val Gln Asn Met Asn Asn
 50                  55                  60
Ala Gly Asp Lys Trp Ser Ala Phe Leu Lys Glu Gln Ser Thr Leu Ala
 65                      70                  75                  80
Gln Met Tyr Pro Leu Gln Glu Ile Gln Asn Leu Thr Val Lys Leu Gln
                     85                  90                  95
Leu Gln Ala Leu Gln Gln Asn Gly Ser Ser Val Leu Ser Glu Asp Lys
                100                 105                 110
Ser Lys Arg Leu Asn Thr Ile Leu Asn Thr Met Ser Thr Ile Tyr Ser
            115                 120                 125
Thr Gly Lys Val Cys Asn Pro Asp Asn Pro Gln Glu Cys Leu Leu Leu
            130                 135                 140
Glu Pro Gly Leu Asn Glu Ile Met Ala Asn Ser Leu Asp Tyr Asn Glu
145                 150                 155                 160
Arg Leu Trp Ala Trp Glu Ser Trp Arg Ser Glu Val Gly Lys Gln Leu
                    165                 170                 175
Arg Pro Leu Tyr Glu Glu Tyr Val Val Leu Lys Asn Glu Met Ala Arg
                180                 185                 190
Ala Asn His Tyr Glu Asp Tyr Gly Asp Tyr Trp Arg Gly Asp Tyr Glu
            195                 200                 205
Val Asn Gly Val Asp Gly Tyr Asp Tyr Ser Arg Gly Gln Leu Ile Glu
210                 215                 220
Asp Val Glu His Thr Phe Glu Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
                260                 265                 270
Arg Phe Trp Thr Asn Leu Tyr Ser Leu Thr Val Pro Phe Gly Gln Lys
            275                 280                 285
Pro Asn Ile Asp Val Thr Asp Ala Met Val Asp Gln Ala Trp Asp Ala
            290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                    325                 330                 335
Gly Asn Val Gln Lys Ala Val Cys His Pro Thr Ala Trp Asp Leu Gly
                340                 345                 350
Lys Gly Asp Phe Arg Ile Leu Met Cys Thr Lys Val Thr Met Asp Asp
            355                 360                 365
Phe Leu Thr Ala His His Glu Met Gly His Ile Gln Tyr Asp Met Ala
            370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                    405                 410                 415
His Leu Lys Ser Ile Gly Leu Leu Ser Pro Asp Phe Gln Glu Asp Asn
                420                 425                 430
Glu Thr Glu Ile Asn Phe Leu Leu Lys Gln Ala Leu Thr Ile Val Gly
            435                 440                 445
Thr Leu Pro Phe Thr Tyr Met Leu Glu Lys Trp Arg Trp Met Val Phe
450                 455                 460
```

Lys Gly Glu Ile Pro Lys Asp Gln Trp Met Lys Lys Trp Trp Glu Met
465                 470                 475                 480

Lys Arg Glu Ile Val Gly Val Val Glu Pro Val His Asp Glu Thr
            485                 490                 495

Tyr Cys Asp Pro Ala Ser Leu Phe His Val Ser Asn Tyr Ser Phe
                500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
                740                 745                 750

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 3
<211> LENGTH: 5
<212> TYPE: PRT
<213> ORGANISM: Artificial Sequence
<220> FEATURE:
<223> OTHER INFORMATION: AIDS core

<400> SEQUENCE: 3

Asn Gly Val Gly Tyr
1               5

```
<210> SEQ ID NO 4
<211> LENGTH: 6
<212> TYPE: PRT
<213> ORGANISM: Artificial Sequence
<220> FEATURE:
<223> OTHER INFORMATION: AIDS peptide

<400> SEQUENCE: 4

Thr Asn Gly Val Gly Tyr
1               5

<210> SEQ ID NO 5
<211> LENGTH: 13
<212> TYPE: PRT
<213> ORGANISM: Artificial Sequence
<220> FEATURE:
<223> OTHER INFORMATION: ADS peptide

<400> SEQUENCE: 5

Gln Ser Tyr Gly Phe Gln Pro Thr Asn Gly Val Gly Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: AIDS peptide

<400> SEQUENCE: 6

Pro Leu Gln Ser Tyr Gly
1               5

<210> SEQ ID NO 7
<211> LENGTH: 7
<212> TYPE: PRT
<213> ORGANISM: Artificial Sequence
<220> FEATURE:
<223> OTHER INFORMATION: SPIDAR peptide

<400> SEQUENCE: 7

Glu Asp Leu Phe Tyr Gln Ser
1               5

<210> SEQ ID NO 8
<211> LENGTH: 6
<212> TYPE: PRT
<213> ORGANISM: Artificial Sequence
<220> FEATURE:
<223> OTHER INFORMATION: mAIDS peptide

<400> SEQUENCE: 8

Thr Gly Gly Val Gly Asp
1               5

<210> SEQ ID NO 9
<211> LENGTH: 6
<212> TYPE: PRT
<213> ORGANISM: Artificial Sequence
<220> FEATURE:
<223> OTHER INFORMATION: SPIDAR peptide

<400> SEQUENCE: 9

Glu Asp Leu Phe Tyr Gln
1               5
```

<210> SEQ ID NO 10
<211> LENGTH: 6
<212> TYPE: PRT
<213> ORGANISM: Artificial Sequence
<220> FEATURE:
<223> OTHER INFORMATION: mSPIDAR peptide

<400> SEQUENCE: 10

Glu Lys Leu Phe Tyr Gly
1               5

<210> SEQ ID NO 11
<211> LENGTH: 25
<212> TYPE: PRT
<213> ORGANISM: Artificial Sequence
<220> FEATURE:
<223> OTHER INFORMATION: AIDS peptide

<400> SEQUENCE: 11

Pro Leu Gln Ser Tyr Gly Phe Gln Pro Thr Asn Gly Val Gly Tyr Gln
1               5                   10                  15

Pro Tyr Arg Val Val Val Leu Ser Phe
            20                  25

<210> SEQ ID NO 12
<211> LENGTH: 24
<212> TYPE: PRT
<213> ORGANISM: Artificial Sequence
<220> FEATURE:
<223> OTHER INFORMATION: SPIDAR peptide

<400> SEQUENCE: 12

Phe Leu Asp Lys Phe Asn His Glu Ala Glu Asp Leu Phe Tyr Gln Ser
1               5                   10                  15

Ser Leu Ala Ser Trp Asn Tyr Asn
            20

<210> SEQ ID NO 13
<211> LENGTH: 17
<212> TYPE: PRT
<213> ORGANISM: Artificial Sequence
<220> FEATURE:
<223> OTHER INFORMATION: Cell penetrating peptide

<400> SEQUENCE: 13

Asp Arg Gln Ile Lys Ile Trp Phe Gln Asn Arg Arg Met Lys Trp Lys
1               5                   10                  15

Lys

<210> SEQ ID NO 14
<211> LENGTH: 23
<212> TYPE: PRT
<213> ORGANISM: Artificial Sequence
<220> FEATURE:
<223> OTHER INFORMATION: CPP AIDS peptide

<400> SEQUENCE: 14

Asp Arg Gln Ile Lys Ile Trp Phe Gln Asn Arg Arg Met Lys Trp Lys
1               5                   10                  15

Lys Thr Asn Gly Val Gly Tyr
            20

<210> SEQ ID NO 15
<211> LENGTH: 23

```
<212> TYPE: PRT
<213> ORGANISM: Artificial Sequence
<220> FEATURE:
<223> OTHER INFORMATION: CPP SPIDAR peptide

<400> SEQUENCE: 15

Asp Arg Gln Ile Lys Ile Trp Phe Gln Asn Arg Arg Met Lys Trp Lys
1               5                   10                  15

Lys Glu Asp Leu Phe Tyr Gln
            20
```

PEPTIDES FOR THE TREATMENT OF COVID-19

RELATED APPLICATIONS

This application claims the benefit of the filing date of U.S. Provisional Patent Application No. 63/078,547, filed Sep. 15, 2020 and U.S. Provisional Patent Application No. 62/704,091, filed Apr. 21, 2020, the contents of which are hereby incorporated by reference.

FEDERALLY SPONSORED RESEARCH AND DEVELOPMENT

This invention was made with Government support of Grant Numbers AG050431, AT010980 and NS108025 awarded by the National Institutes of Health and Grant Number 11K6 BX004982 awarded by the United States Department of Veterans Affairs. The Federal Government has certain rights in this invention.

SEQUENCE LISTING

The instant application contains a Sequence Listing which has been submitted electronically in ASCII format and is hereby incorporated by reference in its entirety. The ASCII copy, created on Dec. 20, 2020, is named R635-US Sequence listing_ST25.txt and is 5 KB in size.

BACKGROUND

COVID-19 is an infectious respiratory illness caused by the virus strain severe acute respiratory syndrome coronavirus 2 (SARS-CoV-2). Common symptoms of COVID-19 are fever, cough, and shortness of breath and with a mortality rate of around 4-5%, it is more than 10 times lethal than the flu. While anyone is susceptible to COVID-19, the ones over 60 or with preexisting conditions, such as hypertension, obesity, asthma, or diabetes, are more vulnerable to severe symptoms (1,2). Until now, no effective therapy is available to tackle this viral pandemic.

Entry of SARS-CoV-2 into the host cells is probably the most important event in COVID-19 disease process. Angiotensin-converting enzyme 2 (ACE2), the main effector of the classical renin-angiotensin system, is a cell surface receptor that is predominant in lung, heart and kidney (3). Although the prototype function of ACE2 is to convert angiotensin II (AngII), a vasoconstrictor, to Ang1-7, a vasodilator, and thereby to play an important role in the pathophysiology of cardiovascular diseases (3,4), recently, ACE2 came to renewed attention due to its requirement by COVID-19 for entering into host cells. It is found that COVID-19 binds to ACE2 via the S protein on its surface (2,5). During infection, the S protein is cleaved into S1 and S2 subunits and the S1 subunit encompasses the receptor-binding domain (RBD). Therefore, this subunit permits COVID-19 to directly attach to the peptidase domain of ACE2 (1,5).

Since ACE2 is a beneficial molecule, either inhibiting or knocking down of ACE2 is not a valid option. Since SARS-CoV-2 binds to angiotensin-converting enzyme 2 (ACE2) for entering into host cells, to target COVID-19 from therapeutic angle, what is needed is an agent that inhibits the association between SARS-CoV-2 spike S1 and ACE-2.

BRIEF SUMMARY

Compositions are provided that include an isolated peptide that inhibits the association between SARS-CoV-2 spike S1 and Angiotensin Converting Enzyme-2 (ACE-2) without inhibiting the activity of ACE-2. In some embodiments, the compositions may comprise an isolated peptide consisting of 15 or fewer amino acids, wherein the peptide comprises at least 75% identity to SEQ ID NO: 3, SEQ ID NO: 4, SEQ ID NO: 5, SEQ ID NO: 6, SEQ ID NO: 7 or SEQ ID NO: 9.

Methods for treating COVID-19 are provided. The methods include administering a first agent to a subject in need thereof, where the first agent comprising an isolated peptide that inhibits the association between SARS-CoV-2 spike S1 and Angiotensin Converting Enzyme-2 (ACE-2) without inhibiting the activity of ACE-2. In some embodiments, the methods include administering a first agent where the first agent comprises an isolated peptide consisting of 15 or fewer amino acids, wherein the peptide comprises at least 75% identity to SEQ ID NO: 3, SEQ ID NO: 4, SEQ ID NO: 5, SEQ ID NO: 6, SEQ ID NO: 7, or SEQ ID NO: 9.

A method of making an in vivo model for COVID-19 is also provided. The method includes administering recombinant SARS-CoV-2 spike S1 protein nasally to an animal.

BRIEF DESCRIPTION OF THE DRAWINGS

FIG. 1A-1K. Designing a peptide for disruption of ACE2 and SARS-CoV-2 Interaction. (A) A rigid-body in silico docked pose of human ACE2 (green) and SARS-CoV-2 spike S1 (magenta). B) Sequence of wild type (SEQ ID NO: 3) and mutated (SEQ ID NO: 7) ACE2-interacting domain of SARS-CoV-2 (AIDS) peptides. Positions of mutations are underlined. C) Inhibition of ACE2 to SARS-CoV-2 expression of IL-6 and IL-1β spike S1 binding by wtAIDS, but not mAIDS, peptide. *$p<0.001$ vs spike S1. Human A549 lung cells pretreated with different concentrations of wtAIDS and mAIDS peptides for 15 min were stimulated with 1 ng/ml recombinant SARS-CoV-2 spike S1 under serum-free condition for 4 h followed by monitoring the mRNA expression of IL-6 (D) and IL-1β (E) by real-time PCR. Similarly, the effect of wtAIDS and mAIDS peptides on the mRNA expression of IL-6 (F, H & J) and IL-1β (G, I & K) was examined in polyIC-(F & G), HIV-1 Tat-(H & I) and flagellin-(J & K) stimulated A549 cells by real-time PCR. $p<0.001$ vs spike S1.

FIG. 2A-2J. Intranasal delivery of wtAIDS peptide reduces fever and decreases lung Infiltration and inflammation in a mouse model of COVID-19. Six-eight week old C57/1BL6 mice (n=6) of both sexes were treated intranasally with wtAIDS or mAIDS peptides (100 ng/mouse/d). After 10 min, mice were intoxicated with recombinant SARS-CoV-2 spike S1 (50 ng/moused) via intranasal route. A) Schematic presentation of experiments. After 7d of treatment, body temperature (B) was monitored by Cardinal Health Dual Scale digital rectal thermometer. Lung sections were analyzed by H&E (C, images of different magnification; D, epithelial cell count; E, neutrophil cell count; F, infiltrated cells as percent of epithelial cells). Cells were counted from two sections of each of five mice (n=5) per group. *$p<0.05$; **$p<0.01$; *$p<0.001$. The mRNA expression of IL-6 (G) and IL-1β (1) was monitored in lung tissues by real-time PCR. IL-6 protein was measured in lung tissue homogenates by ELISA (H) and in serum (J). Results are mean±SEM of six mice per group. *$p<0.05$; $p<0.01$; *$p<0.001$.

FIG. 3A-3K. Intranasal delivery of wtAIDS peptide protects heart function in a mouse model of COVID-19. Six-eight week old C57/1BL6 mice (n=6) of both sexes were treated intranasally with wtAIDS or mAIDS peptides (100 ng/mouse/d). After 10 min, mice were intoxicated with recombinant SARS-CoV-2 spike S1 (50 ng/mouse/d) via intranasal route. After 7d of treatment, heart functions were monitored by non-invasive electrocardiography (ECG) using the PowerLab (ADInstruments) (A, chromatogram of control mice; B, chromatogram of spike S1-intoxicated mice; C, chromatogram of (spike S1+wtAIDS)-treated mice; D, chromatogram of (spike S1+mAIDS)-treated mice; E, heart rate; F, RR interval; G, JT interval; H, R amplitude; I, heart rate variability; J, QRS interval; K, QT interval). Results are mean±SEM of six mice per group. *$p<0.05$; $p<0.01$; *$p<0.001$.

FIG. 4A-4C. Dose-dependent Induction of IL-6 and IL-1β by recombinant SARS-CoV-2 spike S1 In human A549 lung cells. Human A549 lung cells were stimulated with different doses of recombinant SARS-CoV-2 spike S1 under serum-free condition for 4 h followed by monitoring the mRNA expression of IL-6 and IL-1β by semi-quantitative RT-PCR (A) and real-time PCR (B, IL-6; C, IL-1β). In parallel experiment, cells were also stimulated with boiled SARS-CoV-2 spike S1. In this case, SARS-CoV-2 spike S1 was boiled for 5 min. Results are mean±SD of three independent experiments. ***$p<0.001$.

Figure 5A:
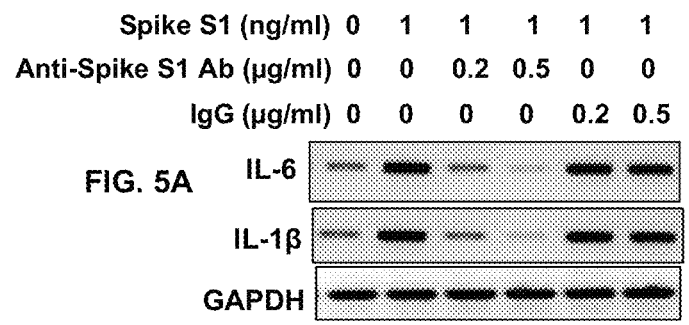
Figure 5B:
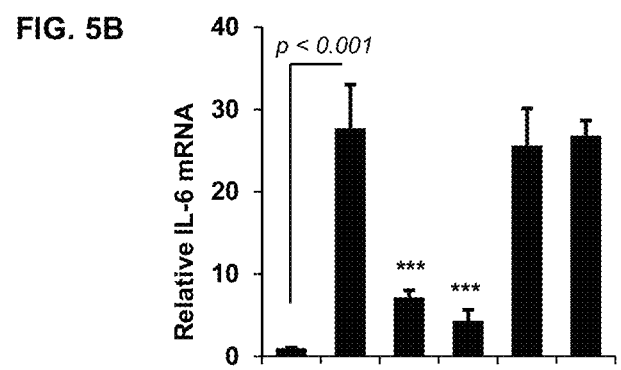
Figure 5C:
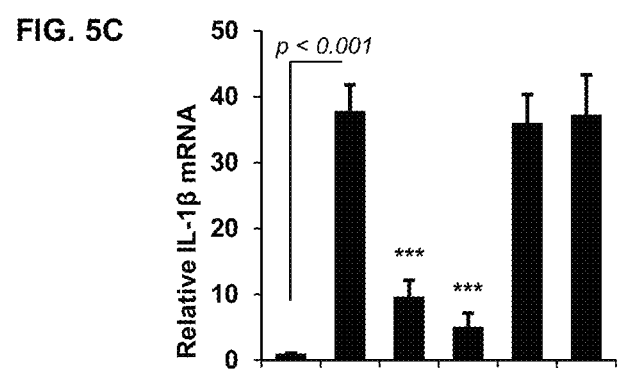
Figure 6A:
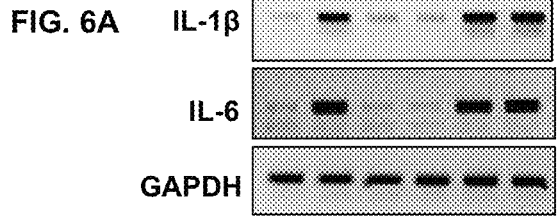
Figure 6B:
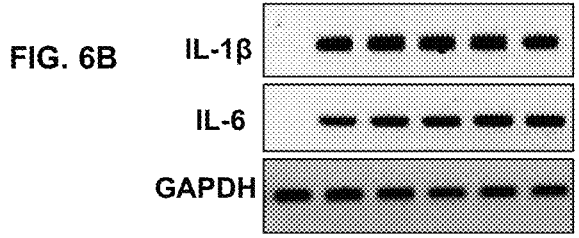
Figure 6C:
Figure 6D:
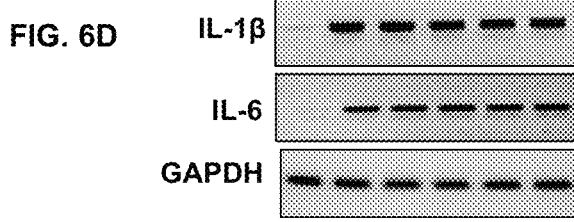

FIG. 5A-5C. Suppression of SARS-CoV-2 spike S1-mediated expression of IL-6 and IL-1β in human A549 lung cells by neutralizing antibodies against spike S1. Human A549 lung cells pretreated with different concentrations of either anti-spike S1 antibody or control IgG for 5 min were stimulated with 1 ng/ml recombinant SARS-CoV-2 spike S1 under serum-free condition for 4 h followed by monitoring the mRNA expression of IL-6 and IL-1β by semi-quantitative RT-PCR (A) and real-time PCR (B, IL-6; C, IL-1β). Results are mean±SD of three independent experiments. ***$p<0.001$.

FIG. 6A-6D. Effect of wtAIDS and mAIDS peptides on the mRNA expression of IL-6 and IL-1β In SARS-CoV-2 spike S1-, poly IC-, HIV tat-, and flagellin-stimulated human A549 lung cells. Human A549 lung cells pretreated with different concentrations of wtAIDS and mAIDS peptides for 15 min were stimulated with recombinant SARS-CoV-2 spike S1 (A), polyIC (B), HIV-1 Tat-(C), and flagellin (D) under serum-free condition for 4 h followed by monitoring the mRNA expression of IL-6 and IL-1β by semi-quantitative RT-PCR. Results represent three independent experiments.

Figure 7:
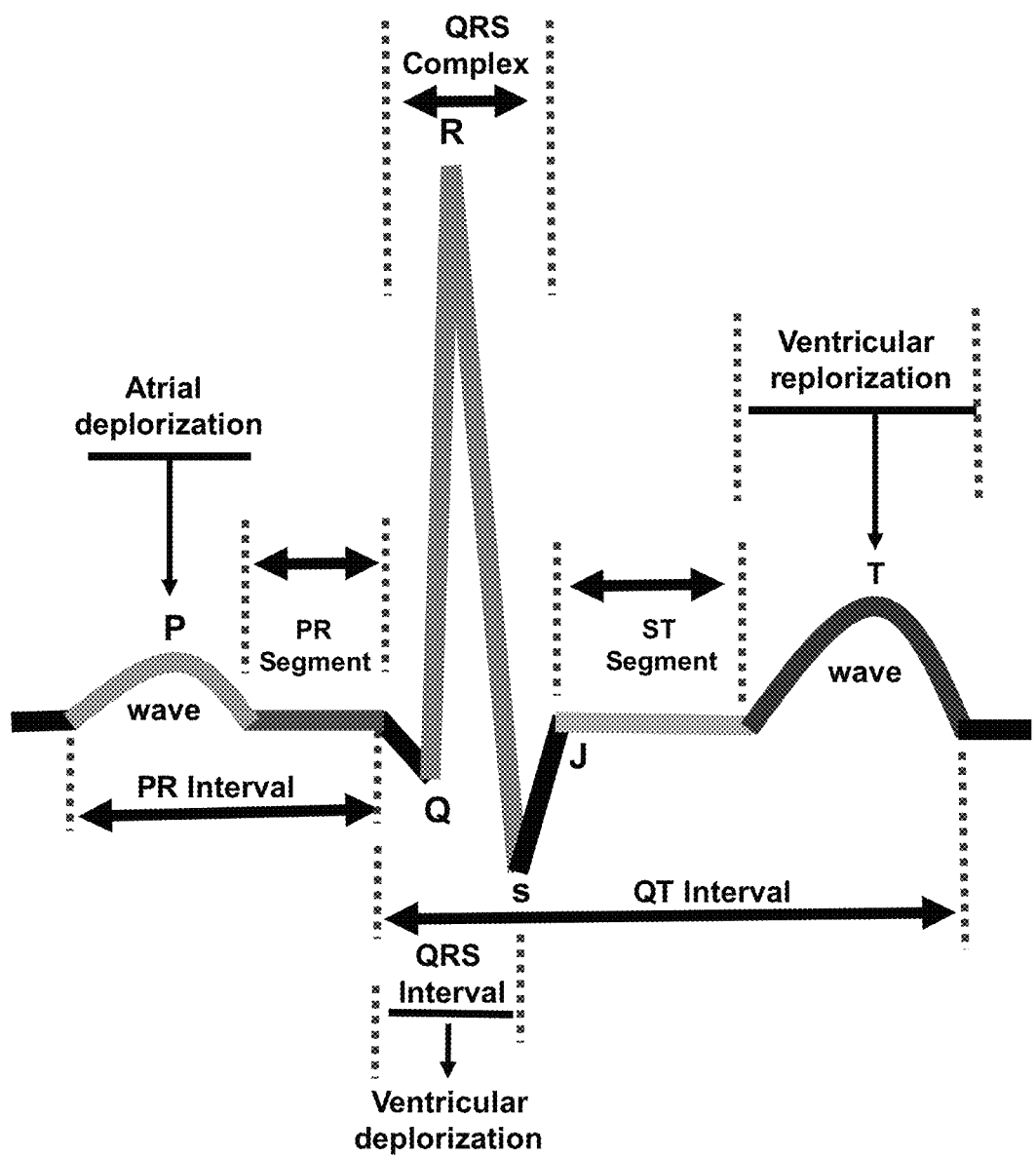
Figure 8E:
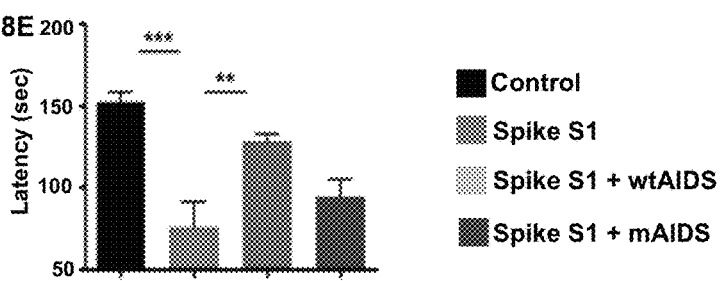
Figure 11A:
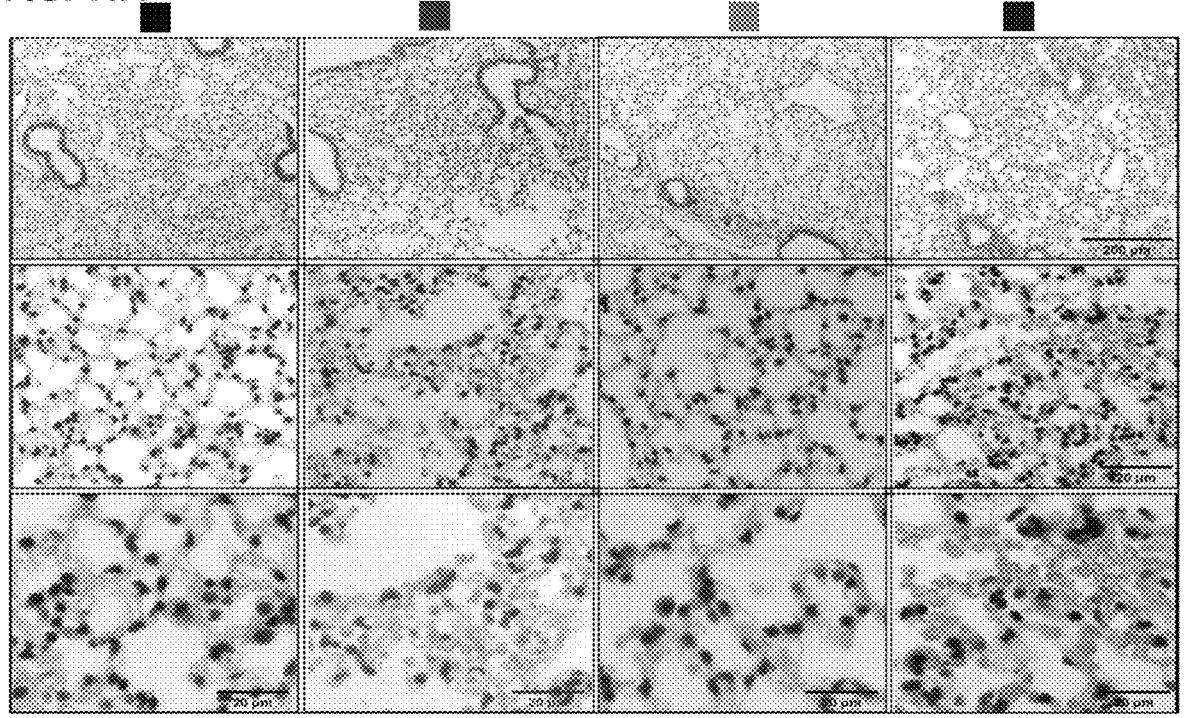
Figure 11B:
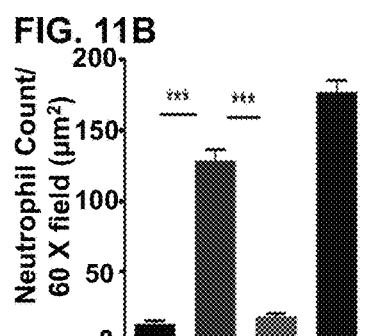
Figure 11C:
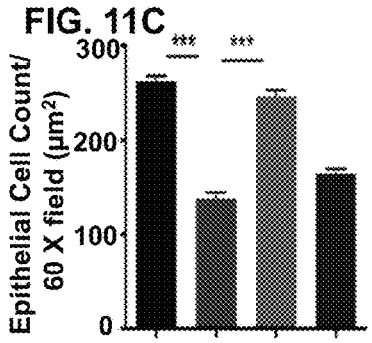
Figure 11D:
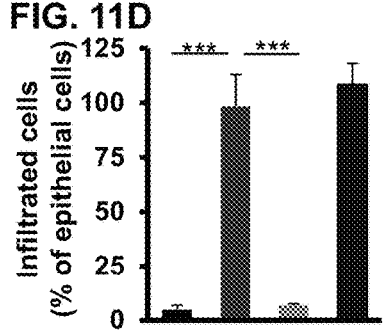
Figure 11E:
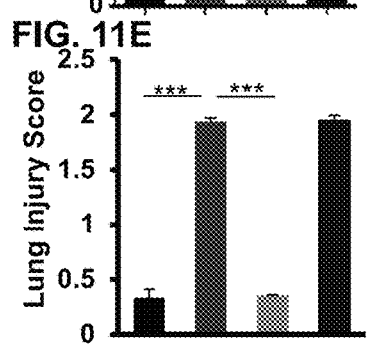
Figure 13A:
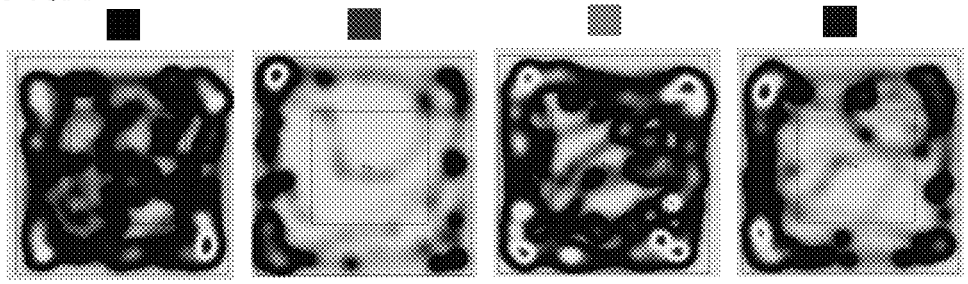
Figure 13B:
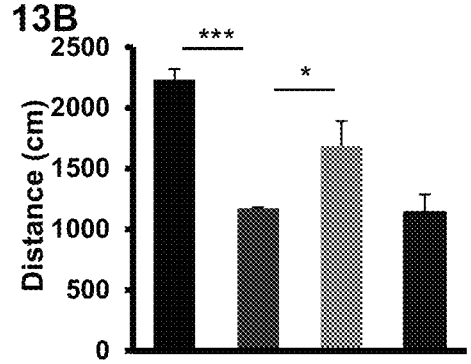
Figure 13C:
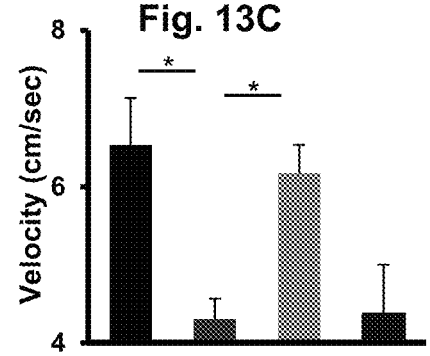
Figure 13D:
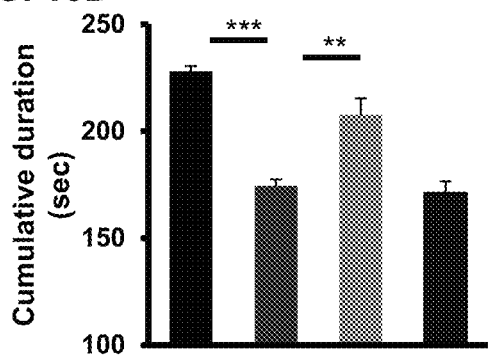
Figure 13E:
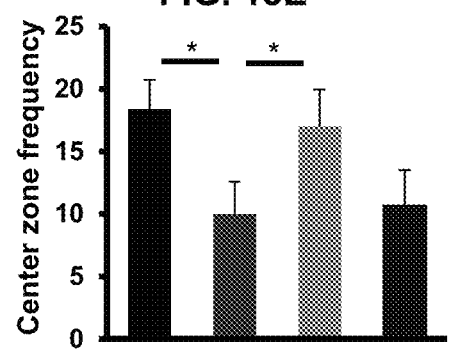
Figure 13F:
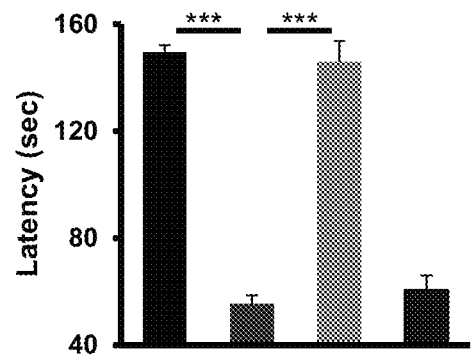

FIG. 7. Schematic presentation of different cardiac parameters.

FIG. 8A-8E. Intranasal delivery of wtAIDS peptide improves locomotor activities in a mouse model of COVID-19. Six-eight week old C57/1BL6 mice (n=6) of both sexes were treated intranasally with wtAIDS or mAIDS peptides (100 ng/mouse/d). After 10 min, mice were intoxicated with recombinant SARS-CoV-2 spike S1 (50 ng/mouse/d) via intranasal route. After 7d of treatment, mice were tested for general locomotor activities (A, heat map; B, distance travelled; C, velocity; D, cumulative duration; E, rotorod latency). Results are mean±SEM of six mice per group. *$p<0.05$; $p<0.01$; *$p<0.001$.

FIG. 9A-9C. Designing of Spike S1-Interacting Domain of ACE2 Receptor (SPIDAR) peptide for disruption of ACE2 and SARS-CoV-2 Interaction. (A) A rigid-body in silico docked pose of human ACE2 (green) and SARS-CoV-2 spike S1 (magenta). B) Sequence of wild type (SEQ ID NO: 8) and mutated (SEQ ID NO: 9) SPIDAR peptides. Positions of mutations are underlined. C) Inhibition of ACE2 to SARS-CoV-2 spike S1 binding by wtSPIDAR, but not mSPIDAR, peptide. *$p<0.05$; ***$p<0.001$ vs spike S1.

FIG. 10A-10G. Intranasal delivery of wtSPIDAR decreases lung Inflammation and reduces fever in a mouse model of COVID-19. Six-eight week old C57/1BL6 mice (n=5) of both sexes were intoxicated with recombinant SARS-CoV-2 spike S1 (50 ng/mouse/d) via intranasal route. After 5 d of treatment, when all mice displayed a body temperature of more than 100° F., mice were treated intranasally with wtSPIDAR or mSPIDAR (100 ng/mouse/d). A) Schematic presentation of experiments. B) After 7d of treatment, the mRNA expression of IL-6 (B) and IL-1β (C) in lung by real-time PCR. IL-6 protein was measured in lung tissue homogenates by ELISA (D). Levels of IL-6 (E) and CRP (F) were also quantified in serum by ELISA. Body temperature (G) was monitored by Cardinal Health Dual Scale digital rectal thermometer. Results are mean±SEM of 5 mice per group. ***$p<0.001$; NS, not significant.

FIG. 11A-11E. Intranasal delivery of wtSPIDAR decreases lung Infiltration in a mouse model of COVID-19. Six-eight week old C57/1BL6 mice (n=5) of both sexes were intoxicated with recombinant SARS-CoV-2 spike S1 (50 ng/mouse/d) via intranasal route. After 5 d of treatment, when all mice displayed a body temperature of more than 100° F., mice were treated intranasally with wtSPIDAR or mSPIDAR (100 ng/mouse/d). After 7d of treatment, lung sections were analyzed by H&E (A, images of different magnification; B, neutrophil cell count; C, epithelial cell count; D, infiltrated cells as percent of epithelial cells; E, lung injury score). Cells were counted from two sections of each of five mice (n=5) per group. Results are mean±SEM of 5 mice per group. ***$p<0.001$.

FIG. 12A-12J. Intranasal delivery of wtSPIDAR protects heart functions in a mouse model of COVID-19. Six-eight week old C57/1BL6 mice (n=5) of both sexes were intoxicated with recombinant SARS-CoV-2 spike S1 (50 ng/mouse/d) via intranasal route. After 5 d of treatment, when all mice displayed a body temperature of more than 100° F., mice were treated intranasally with wtSPIDAR or mSPIDAR (100 ng/mouse/d). After 7d of treatment, heart functions were monitored by non-invasive electrocardiography (ECG) using the PowerLab (ADInstruments) [A, chromatogram of control mice; B, chromatogram of spike S1-intoxicated mice; C, chromatogram of (spike S1+wtSPIDAR)-treated mice; D, chromatogram of (spike S1+mSPIDAR)-treated mice; E, heart rate; F, QRS interval; G, QT interval; H, RR interval; I, heart rate variability]. J) Serum LDH was quantified using an assay kit from Sigma. Results are mean±SEM of 5 mice per group. *$p<0.05$; $p<0.01$; *$p<0.001$.

FIG. 13A-13F. Intranasal delivery of wtSPIDAR Improves locomotor activities in a mouse model of COVID-19. Six-eight week old C57/1BL6 mice (n=5) of both sexes were intoxicated with recombinant SARS-CoV-2 spike S1 (50 ng/mouse/d) via intranasal route. After 5 d of treatment, when all mice displayed a body temperature of more than 100° F., mice were treated intranasally with wtSPIDAR or mSPIDAR (100 ng/mouse/d). After 7d of treatment, mice were tested for general locomotor activities (A, heat map; B, distance travelled; C, velocity; D, cumulative duration; E, center zone frequency; F, rotorod latency). Results are mean±SEM of 5 mice per group. *$p<0.05$; $p<0.01$; *$p<0.001$.

DETAILED DESCRIPTION

The embodiments disclosed below are not intended to be exhaustive or to limit the scope of the disclosure to the precise form in the following description. Rather, the embodiments are chosen and described as examples so that others skilled in the art may utilize its teachings.

Compositions and methods for specific targeting of the binding between ACE2 and SARS-CoV-2 are provided. Recombinant peptides were designed corresponding to the ACE2-interacting domain of SARS-CoV-2 spike S1 (AIDS) that inhibited the binding between ACE2 and SARS-CoV-2 spike S1. Methods of treating COVID-19 using the peptides described herein are also provided. In some embodiments, the recombinant peptides specifically reduced spike S1-mediated induction of IL-6 and IL-1β in lung cells without modulating double-stranded RNA (poly IC)- and HIV-1 Tat-mediated expression of IL-6 and IL-1p.

An in vivo model of COVID-19 is also provided.

The term "amino acid" refers, in particular, to any one of the 20 standard proteinogenic a-amino acids (i.e., Ala, Arg, Asn, Asp, Cys, Glu, Gin, Gly, His, He, Leu, Lys, Met, Phe, Pro, Ser, Thr, Trp, Tyr, and Val) but also to non-proteinogenic and/or non-standard a-amino acids (such as, e.g., omithine, citrulline, homolysine, pyrrolysine, 4-hydroxyproline, a-methylalanine (i.e., 2-aminoisobutyric acid), norvaline, norleucine, terleucine (tert-leucine), labionin, or an alanine or glycine that is substituted at the side chain with a cyclic group such as, e.g., cyclopentylaianine, cyclohexylalanine, phenylalanine, naphthylalanine, pyridylalanine, thienylalanine, cyclohexylglycine, or phenylglycine) as well as β-amino acids (e.g., β-alanine), γ-amino acids (e.g., γ-aminobutyric acid, isoglutamine, or statine) and/or δ-amino acids as well as any other compound comprising at least one carboxylic acid group and at least one amino group. Unless defined otherwise, an "amino acid" preferably refers to an a-amino acid, more preferably to any one of the 20 standard proteinogenic a-amino acids (which can be present as the L-isomer or the D-isomer, and are preferably present as the L-isomer).

The terms "peptide" and "polypeptide", are used herein interchangeably and refer to a polymer of two or more amino acids linked via amide bonds that are formed between an amino group of one amino acid and a carboxyl group of another amino acid. the term peptide or polypeptide, it is meant to include the peptide or polypeptide itself, as well as any physiologically acceptable salts thereof, or any chemically modification made thereto, which would be apparent or known to a person of ordinary skill in the art. The amino acids comprised in the peptide or polypeptide, which are also referred to as amino acid residues, may be selected from the 20 standard proteinogenic a-amino acids (i.e., Ala, Arg, Asn, Asp, Cys, Glu, Gin, Gly, His, Iie, Leu, Lys, Met, Phe, Pro, Ser, Thr, Trp, Tyr, and Val) but also from non-proteinogenic and/or non-standard a-amino acids (such as, e.g., omithine, citrulline, homolysine, pyrrolysine, 4-hydroxyproline, a-methylalanine (i.e., 2-aminoisobutyric acid), norvaline, nordeucine, terleucine (tert-leucine), labionin, or an alanine or glycine that is substituted at the side chain with a cyclic group such as, e.g., cyclopentylalanine, cydohexylalanine, phenylalanine, naphthylalanine, pyridylalanine, thienylalanine, cydohexylglycine, or phenylglycine) as well as β-amino acids (e.g., β-alanine), γ-amino acids (e.g., γ-aminobutyric acid, isogiutamine, or statine) and δ-amino acids. Preferably, the amino acid residues comprised in the peptide or polypeptide are selected from a-amino acids, more preferably from the 20 standard proteinogenic a-amino acids (which can be present as the L-isomer or the D-isomer, and are preferably all present as the L-isomer). The peptide or polypeptide may be unmodified or may be modified, e.g., at its N-terminus, at its C-terminus and/or at a functional group in the side chain of any of its amino acid residues (particularly at the side chain functional group of one or more Lys, His, Ser, Thr, Tyr, Cys, Asp, Glu, and/or Arg residues). Such modifications may include, e.g., the attachment of any of the protecting groups described for the corresponding functional groups in: Wuts PG & Greene TW, Greene's protective groups in organic synthesis, John Wiley & Sons, 2006. Such modifications may also include the covalent attachment of one or more polyethylene glycol (PEG) chains (forming a PEGylated peptide or polypeptide), the glycosylation and/or the acylation with one or more fatty acids (e.g., one or more $C_{8\text{-}30}$ alkanoic or alkenoic acids; forming a fatty acid acyiated peptide or polypeptide). Moreover, such modified peptide or proteins may also include peptidomimetics, provided that they contain at least two amino acids that are linked via an amide bond (formed between an amino group of one amino acid and a carboxyl group of another amino acid). The amino acid residues comprised in the peptide or polypeptide may, e.g., be present as a linear molecular chain (forming a linear peptide or protein) or may form one or more rings (corresponding to a cyclic peptide or polypeptide). The peptide or polypeptide may also form oligomers consisting of two or more identical or different molecules.

The term "identity" refers to the overall relatedness between polymeric molecules, e.g., between peptides or polypeptides. Methods for the calculation of a percent identity as between two provided polypeptide sequences are known. Calculation of the percent identity of two polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of an algorithm available for comparison of amino acid or nucleic acid sequences, comprising those available in commercial computer programs is BLASTN for nucleotide sequences and BLASTP, gapped BLAST, and PSI-BLAST for amino acid sequences. Exemplary programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence.

The term "subject" or "patient" as used herein, refers to a mammal, in some aspects a human.

A "therapeutically effective amount," "effective dose," "effective amount," or "therapeutically effective dosage" of a therapeutic agent, e.g., a peptide, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The therapeutic agent may inhibit (lessen the severity of or eliminate the occurrence of) and/or prevent a disorder, and/or any one of the symptoms of the disorder.

The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

"Treating", "treat", or "treatment" within the context of the instant disclosure, means an alleviation of symptoms associated with a disorder or disease, or halt of further progression or worsening of those symptoms, or prevention or prophylaxis of the disease or disorder. For example, within the context of this disclosure, successful treatment may include an alleviation of symptoms related to COVID-19. The treatment may include administering an effective amount of a peptide to the subject that results in an alleviation of symptoms associated with a disorder or disease, or halt of further progression or worsening of those symptoms, or prevention or prophylaxis of the disease or disorder.

In some embodiments, practice of the present disclosure will employ, unless otherwise indicated, conventional techniques of molecular biology, immunology, microbiology, cell biology and recombinant DNA, which are within the skill of the art. See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.)

Recombinant Peptides

Recombinant peptides were designed corresponding to the ACE2-interacting domain of SARS-CoV-2 spike S1 (AIDS) and the spike S1-Interacting Domain of ACE2 Receptor (SPIDAR) that inhibited the binding between ACE2 and SARS-CoV-2 spike S1. The recombinant peptides used herein may be constructed solely of natural amino acids. Alternatively, the recombinant peptides may include non-natural amino acids including, but not limited to, modified amino acids. Modified amino acids include natural amino acids which have been chemically modified to include a group or groups not naturally present on the amino acid. The recombinant peptides may additionally include D-amino adds. Still further, the recombinant peptides may include amino acid analogs.

The SARS-CoV-2 spike S1 is shown in SEQ ID NO: 1.

(SEQ ID NO: 1)
SLVSLLSVLL MGCVAETGTQ CVNLTTRTQL PPAYTNSFTR

GVYYPDKVFR SSVLHSTQDL FLPFFSNVTW FHAIHVSGTN

GTKRFDNPVL PFNDGVYFAS TEKSNIIRGW IFGTTLDSKT

QSLLIVNNAT NVVIKVCEFQ FCNDPFLGVY YHKNNKSWME

SEFRVYSSAN NCTFEYVSQP FLMDLEGKQG NFKNLREFVF

KNIDGYFKIY SKHTPINLVR DLPQGFSALE PLVDLPIGIN

ITRFQTLLAL HRSYLTPGDS SSGWTAGAAA YYVGYLQPRT

FLLKYNENGT ITDAVDCALD PLSETKCTLK SFTVEKGIYQ

ISNFRVQPIE SIVRFPNITN LCPFGEVFNA TRFASVYAWN

RKRISNCVAD YSVLYNSASF STFKCYGVSP TKLNDLCFTN

VYADSFVIRG DEVRQIAPGQ TGKIADYNYK LPDDFTGCVI

AWNSNNLDSK VGGNYNYLYR LFRKSNLKPF ERDISTEIYQ

AGSTPCNGVE GFNCYFPLQS YGFQPTNGVG YQPYRVVVLS

FELLHAPATV CGPKKSTNLV KNKCVNFNFN GLTGTGVLTE

SNKKFLPFQQ FGRDIADTTD AVRDPQTLEI LDITPCSFGG

VSVITPGTNT SNQVAVLYQD VNCTEVPVAI HADQLTPTWR

VYSTGSNVFQ TRAGCLIGAE HVNNSYECDI PI

The Angiotensin Converting Enzyme 2 (ACE2) is shown in SEQ ID NO: 2.

(SEQ ID NO: 2)
MSSSSWLLLS LVAVTAAQST IEEQAKTFLD KFNHEAEDLF

YQSSLASWNY NTNITEENVQ NMNNAGDKWS AFLKEQSTLA

QMYPLQEIQN LTVKLQLQAL QQNGSSVLSE DKSKRLNTIL

NTMSTIYSTG KVCNPDNPQE CLLLEPGLNE IMANSLDYNE

RLWAWESWRS EVGKQLRPLY EEYVVLKNEM ARANHYEDYG

DYWRGDYEVN GVDGYDYSRG QLIEDVEHTF EEIKPLYEHL

HAYVRAKLMN AYPSYISPIG CLPAHLLGDM WGRFWTNLYS

LTVPFGQKPN IDVTDAMVDQ AWDAQRIFKE AEKFFVSVGL

PNMTQGFWEN SMLTDPGNVQ KAVCHPTAWD LGKGDFRILM

CTKVTMDDFL TAHHEMGHIQ YDMAYAAQPF LLRNGANEGF

HEAVGEIMSL SAATPKHLKS IGLLSPDFQE DNETEINFLL

```
KQALTIVGTL PFTYMLEKWR WMVFKGEIPK DQWMKKWWEM

KREIVGVVEP VPHDETYCDP ASLFHVSNDY SFIRYYTRTL

YQFQFQEALC QAAKHEGPLH KCDISNSTEA GQKLFNMLRL

GKSEPWTLAL ENVVGAKNMN VRPLLNYFEP LFTWLKDQNK

NSFVGWSTDW SPYADQSIKV RISLKSALGD KAYEWNDNEM

YLFRSSVAYA MRQYFLKVKN QMILFGEEDV RVANLKPRIS

FNFFVTAPKN VSDIIPRTEV EKAIRMSRSR INDAFRLNDN

SLEFLGIQPT LGPPNQPPVS IWLIVFGVVM GVIVVGIVIL

IFTGIRDRKK KNKARSGENP YASIDISKGE NNPGFQNTDD

VQTSF
```

Recombinant peptides that inhibit the binding between ACE2 and SARS-CoV-2 spike S1 may include a core sequence of NGVGY (SEQ ID NO: 3) and peptides having at least 75%, at least 80%, at least 90%, at least 95%, or 100% identity; e.g., 75-80%, 80-85%, 85-90%, 85-95%, 85-100%, 90-95%, 90-100%, or 95-100%) thereto. In some embodiments, the recombinant peptide may have at least 75%, at least 80%, at least 90%, at least 95%, or 100% identity; e.g., 75-80%, 80-85%, 85-90%, 85-95%, 85-100%, 90-95%, 90-100%, or 95-100%) identity to a core sequence TNGVGY (SEQ ID NO: 4). In some embodiments, the recombinant peptide may have at least 75%, at least 80%, at least 90%, at least 95%, or 100% identity; e.g., 75-80%, 80-85%, 85-90%, 85-95%, 85-100%, 90-95%, 90-100%, or 95-100%) identity to QSYGFQPTNGVGY (SEQ ID NO: 5). In some embodiments, the core sequence of SEQ ID NO: 2 targets amino acids 501-505 of the SARS-CoV-2 spike S1 protein. In yet other embodiments, the recombinant peptides may have at least 75%, at least 80%, at least 90%, at least 95%, or 100% identity; e.g., 75-80%, 80-85%, 85-90%, 85-95%, 85-100%, 90-95%, 90-100%, or 95-100%) identity to a core sequence PLQSYG (SEQ ID NO: 6). In yet other embodiments, the recombinant peptides may have at least 75%, at least 80%, at least 90%, at least 95%, or 100% identity; e.g., 75-80%, 80-85%, 85-90%, 85-95%, 85-100%, 90-95%, 90-100%, or 95-100%) identity to a core EDLFYQS (SEQ ID NO: 7). In yet other embodiments, the recombinant peptides may have at least 75%, at least 80%, at least 90%, at least 95%, or 100% identity; e.g., 75-80%, 80-85%, 85-90%, 85-95%, 85-100%, 90-95%, 90-100%, or 95-100%) identity to a core EDLFYQ (SEQ ID NO: 9). In some embodiments, one, two, three or more recombinant peptides may be used together. By way of non-limiting example, the recombinant peptides of SEQ ID NO: 3, SEQ ID NO: 4, and/or SEQ ID NO: 5 may be combined with SEQ ID NO: 6, SEQ ID NO: 7 and/or SEQ ID NO: 9 and delivered to a subject. In some embodiments, the recombinant peptides disclosed herein may be in a composition comprising an isolated peptide consisting of 15 or fewer amino acids.

In some embodiments, the recombinant peptides disclosed herein may be in a composition comprising an isolated peptide consisting of 15 or fewer amino acids and include a core sequence of 5, 6 or 7 amino acids plus up to 10, 9 or 8 additional amino acids, respectively, added to the N-terminus or C-terminus or both the N-terminus and the C-terminus of the core sequence. In some embodiments, the recombinant peptides disclosed herein may be in a composition comprising an isolated peptide consisting of 15 or fewer amino acids and include a core sequence of 5, 6 or 7 amino acids plus up to 10, 9 or 8 additional amino acids, respectively, added to the N-terminus or C-terminus or both the N-terminus and the C-terminus of the core sequence (shown in bold) in consecutive order from the core sequence based on PLQSYGFQPTNGVGYQPYRWVLSF (SEQ ID NO: 11) or FLDKFNHEAEDLFYQSSLASWNYN (SEQ ID NO: 12) and extending in either direction for a total of 15 or fewer amino acids. In some embodiments, the recombinant peptides disclosed herein may be in a composition comprising an isolated peptide consisting of 15 or fewer amino acids and include a core sequence of 5, 6 or 7 amino acids plus fewer than 10, 9 or 8 additional amino acids, respectively, added to the N-terminus or the C-terminus or both the N-terminus and the C-terminus of the core sequence. In some embodiments, the recombinant peptide consists essentially of SEQ ID NO: 3, SEQ ID NO: 4, SEQ ID NO: 5, SEQ ID NO: 6, SEQ ID NO: 7 and/or SEQ ID NO: 9 or SEQ ID NO: 3, SEQ ID NO: 4, SEQ ID NO: 5, SEQ ID NO: 6, SEQ ID NO: 7 and/or SEQ ID NO: 9 having one or two amino acid variations, in the core sequence or added to the N-terminus or the C-terminus or both the N-terminus and the C-terminus of the core sequence.

In some embodiments, the composition may include an addition peptide to clear SARS-CoV-2 from central nervous system (CNS). The additional peptide may facilitate penetrance of the isolated peptide that inhibits the binding between ACE2 and SARS-CoV-2 spike S1 into the CNS. In some embodiments the additional peptide may be from antennapedia homeodomain. In some embodiments, the cell penetrating peptide may be DRQIKIWFQNRRMKWKK (SEQ ID NO: 13). The cell penetrating peptide may be added to the N-terminus or the C-terminus of any of the peptides described above that inhibit the binding between ACE2 and SARS-CoV-2 spike S1.

By way of non-limiting example, the AIDS peptide for clearing SARS-CoV-2 from the brain and spinal cord may be: DRQIKIWFQNRRMKWKKTNGVGY (SEQ ID NO: 14) and the SPIDAR peptide for clearing SARS-CoV-2 from the brain and spinal cord may be: DRQIKIWFQNRRMKWKKEDLFYQ (SEQ ID NO: 15). In some embodiments, any of the AIDS peptide family members may be coupled to the cell penetrating peptide. In some embodiments, any of the SPIDAR peptide family members may be coupled to the cell penetrating peptide.

Pharmaceutical Compositions

The peptides described herein may be used alone or in compositions together with a pharmaceutically acceptable carrier or excipient. Pharmaceutical compositions of the disclosed herein may comprise a therapeutically effective amount of one or more peptides, together with one or more pharmaceutically acceptable carriers. In some embodiments, the peptide is used alone with a pharmaceutically acceptable carrier or excipient such that no other active agent is administered with the peptide.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar;

buffering agents such as magnesium hydroxide and aluminum hydroxide; alginic acid; pyrogen-free water; isotonic saline; Ringers solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

The peptides described herein may be administered to humans and animals in dosage unit formulations containing conventional nontoxic pharmaceutically acceptable carriers, adjuvants, and vehicles as desired.

Methods of formulation are well known in the art and are disclosed, for example, in Remington: The Science and Practice of Pharmacy, Mack Publishing Company, Easton, Pa., 19th Edition (1995). Pharmaceutical compositions for use in the present disclosure can be in the form of sterile, non-pyrogenic liquid solutions or suspensions, coated capsules or lipid particles, lyophilized powders, or other forms known in the art.

Peptides as used herein may be formulated for delivery as a liquid, aerosol or inhalable dry powder. Peptides may be delivered nasally or by inhalation. Liquid aerosol formulations may be nebulized predominantly into particle sizes that can be delivered to the terminal and respiratory bronchioles.

Liquid dosage forms for oral administration include pharmaceutically acceptable emulsions, microemulsions, solutions, suspensions, syrups and elixirs. In addition to the peptide, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the peptide is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The peptides can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the peptide may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a peptide include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this disclosure.

The ointments, pastes, creams and gels may contain, in addition to a peptide, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

The peptides may also be formulated for use as topical powders and sprays that can contain, in addition to the peptide, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches may also be used for providing controlled delivery of a peptide to the body. Such dosage forms can be made by dissolving or dispensing the peptide in the proper medium. Absorption enhancers can also be used to increase the flux of the peptide across the skin. The rate can be controlled by either providing a rate controlling membrane or by dispersing the peptide in a polymer matrix or gel. The peptide can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a peptide, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

Aerosolized formulations of the peptides described herein may be delivered using an aerosol forming device, such as a jet, vibrating porous plate or ultrasonic nebulizer, preferably selected to allow the formation of an aerosol particles having with a mass medium average diameter predominantly between 1 to 5 µm. Further, the formulation preferably has balanced osmolarity ionic strength and chloride concentration, and the smallest aerosolizable volume able to deliver effective dose of the peptide to the site of treatment. Additionally, the aerosolized formulation preferably does not impair negatively the functionality of the airways and does not cause undesirable side effects.

Aerosolization devices suitable for administration of aerosol formulations of the peptide include, for example, jet, vibrating porous plate, ultrasonic nebulizers and energized dry powder inhalers, that are able to nebulize the formulation of the peptide into aerosol particle size predominantly in the size range from 1-5 µm. Predominantly in this application means that at least 70% but preferably more than 90% of all generated aerosol particles are within 1-5 µm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDE-STREAM nebulizers (Medic-Aid Ltd., West Sussex, England), PARI LC and PARI LC STAR jet nebulizers (Pan Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringers solution, U.S.P. and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

A peptide described herein can be administered alone or in combination with other agents, for a possible combination therapy being staggered or given independently of one another. Long-term therapy is equally possible as is adjuvant therapy in the context of other treatment strategies, as described above. Other possible treatments are therapy to maintain the patients status after the initial treatment, or even preventive therapy, for example in patients at risk.

Effective amounts of the peptide generally include any amount sufficient to detectably an inhibition or alleviation of symptoms. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific peptide employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

If the peptide is administered in combination with another compound, the term "amount that is effective" is understood to mean that amount of peptide in combination with the additional compound to achieve the desired effect. In other words, a suitable combination therapy according to the current disclosure encompasses an amount of the peptide and an amount of the additional compound, either of which when given alone at that particular dose would not constitute an effective amount, but administered in combination would be an "amount that is effective".

It will be understood, however, that the total daily usage of the peptide and compositions of the present disclosure will be decided by the attending physician within the scope of sound medical judgment. The specific therapeutically effective dose level for any particular patient will depend upon a variety of factors including the disorder being treated and the severity of the disorder; the activity of the specific peptide employed; the specific composition employed; the age, body weight, general health, sex and diet of the patient; the time of administration, route of administration, and rate of excretion of the specific peptide employed; the duration of the treatment; drugs used in combination or coincidental with the specific peptide employed; and like factors well known in the medical arts.

The dose of a peptide to be administered to warm-blooded animals, for example humans of approximately 70 kg body weight, is preferably from approximately 3 mg to approximately 5 g, more preferably from approximately 10 mg to approximately 1.5 g, most preferably from about 100 mg to about 1000 mg per person per day, divided preferably into 1 to 3 single doses which may, for example, be of the same size. Usually, children receive half of the adult dose.

In Vivo Model of SARS-CoV-2

An in vivo model for COVID-19 is included herein. The in vivo model is a virus free model that develops one or more symptoms of COVID-19 including but not limited to fever, augmented lung inflammation, increased infiltration of neutrophils into the lungs, decreased heart function, and impaired locomotor activities relative to a control animal. The in vivo model is prepared by administering recombinant SARS-CoV-2 spike S1 protein nasally to an animal. By way of non-limiting example, the recombinant SARS-CoV-2 spike S1 may be SEQ ID NO; 1 although other sequence variants of SARS-CoV-2 spike S1 may also be used. In some embodiments, the recombinant SARS-CoV-2 spike S1 may be delivered nasally to one or both nostrils of the animal. In some embodiments, the recombinant SARS-CoV-2 spike S1 may be delivered by inhalation. In some embodiments, the recombinant SARS-CoV-2 spike S1 protein is delivered in a saline solution.

EXAMPLES

Example 1

Results

Designing of a peptide corresponding to the ACE2-interacting domain of SARS-CoV-2 (AIDS): Since there is no specific treatment for COVID-19, from the therapeutic angle, we decided to target the interaction between SARS-CoV-2 and its receptor ACE2. The receptor-binding domain (RBD) of SARS-CoV-2 spike S1 is involved in the interaction with ACE2[6]. Therefore, we applied rigid-body protein-protein interaction tool to model the interaction between RBD of spike protein S1 subunit and ACE2. As evident from our in silico modeling analysis, the docked pose of ACE2 and S1 RBD complex revealed a strong H-bond between Asn501 of spike S1 and Lys353 of ACE2. In addition, Tyr505 of spike S1 exhibited a hydrophobic interaction with Gln42 and the side chain of Lys353 of ACE2 (FIG. 1A). Therefore, we designed a hexapeptide (FIG. 1B) corresponding to the ACE2-interacting domain of SARS-CoV-2 (AIDS) from the RBD of S1 subunit to unsettle the interaction between SARS-CoV-2 and ACE2:

```
Wild type (wt) AIDS:
                                    (SEQ ID NO: 4)
500TNGVGY505

Mutated (m) AIDS:
                                    (SEQ ID NO: 8)
500TGGVGD505
```

Positions of mutations are underlined. Next, to examine whether wtAIDS peptide inhibits the binding of ACE2 with SARS-CoV-2 spike S1, we employed chemiluminescence-based ACE2:SARS-CoV-2 spike S1 binding using an assay kit (catalog #79936; BPS Bioscience). As evident from FIG. 1C, SARS-CoV-2 spike S1 binding to immobilized ACE2 was strongly inhibited by wtAIDS peptide. However, no such inhibition was found with mAIDS peptide (FIG. 1C), indicating the specificity of the effect.

AIDS peptide inhibits lung cell inflammation induced by SARS-CoV-2 spike S1, but not double-stranded RNA (poly IC), HIV-1 Tat, and bacterial flagellin: Pulmonary inflammation ultimately leading to acute lung injury is becoming a hallmark of COVID-19 patients visiting ICU[7]. In addition to COVID-19, pulmonary complications are also evident in different bacterial and viral infections[8,9]. Therefore, we investigated if AIDS peptide was capable of suppressing the expression of proinflammatory molecules in human A549 lung cells induced by different stimuli. A549 cells pretreated with different concentrations of wtAIDS and mAIDS peptides for 15 min were stimulated with recombinant SARS-CoV-2 spike S1, poly IC, HIV-1 Tat, and bacterial flagellin. At first, we examined whether recombinant SARS-CoV-2 spike S1 was capable of inducing proinflammatory cytokines in A549 lung cells. Dose-dependent analysis showed that SARS-CoV-2 spike S1 was very potent in inducing proinflammatory cytokines and that spike S1 even at a dose of 0.2 ng/ml significantly induced the mRNA expression of IL-6 and IL-1β in lung cells with maximum induction at 1 ng/ml (FIG. 1A-C). Inability of boiled recombinant SARS-CoV-2 spike S1 to induce the expression of IL-6 and IL-1β in A549 cells (FIGS. 1A-C) and neutralization of SARS-CoV-2 spike S1-mediated expression of these cytokines by anti-SARS-CoV-2 spike S1 antibody (FIG. 2A-C) suggest that the induction of proinflammatory molecules in lung cells is due to SARS-CoV-2 spike S1 protein. Moreover, these results also suggest that the so-called "cytokine storm" seen in some COVID-19 patients may be due to the function of spike S1.

Similarly, poly IC (FIG. 1F-G & FIG. 3B), HIV-1 Tat (FIG. 1H-I & FIG. 3C), and flagellin (FIG. 1J-K & FIG. 3D) also increased the expression of IL-6 and IL-1β in A549 cells. However, wtAIDS peptides inhibited SARS-CoV-2 spike S1-mediated induction of IL-6 and IL-1β in A549 cells (FIG. 1D-E & FIG. 3A). In contrast, wtAIDS peptides remained unable to decrease the expression of IL-6 and IL-1β induced by poly IC (FIG. 1F-G & FIG. 3B), HIV-1 Tat (FIG. 1H-I & FIG. 3C), and flagellin (FIG. 1J-K & FIG. 3D). These results were specific as mAIDS peptides had no effect on the expression of IL-6 and IL-1β induced by any of the stimuli used.

Intranasal administration of SARS-CoV-2 spike S1 causes fever and lung inflammation: Protection by wtAIDS peptide: One of the most common symptoms of COVID-19 is fever 2.10. Interestingly, daily intranasal administration of SARS-CoV-2 spike S1 at a very low dose (FIG. 2A) led to increase in body temperature (FIG. 2B). Since shortness of breath is an important issue of COVID-19 patients in the ICU[11], we also examined if intranasal administration of SARS-CoV-2 spike S1 could mimic some of the pulmonary features of COVID-19. We found widespread infiltration of neutrophils into the lungs of SARS-CoV-2 spike S1-intoxicated mice as compared to control mice receiving only saline (FIG. 2C). Cell counting indicated a loss of epithelial cells (FIG. 2D) and a marked increase in neutrophil infiltration (FIG. 2E-F) into the lungs after SARS-CoV-2 spike S1-intoxication. In some COVID-19 patients, disease progression leads to "cytokine storm" and among these cytokines, IL-6 plays an important role as elevated levels of IL-6 closely correlates to critical illness[12]. Therefore, we examined the level of IL-6 and found marked increase in IL-6 mRNA (FIG. 2G) and protein (FIG. 2H) as well as IL-1β mRNA (FIG. 2I) in lungs of SARS-CoV-2 spike S1-intoxicated mice as compared to control mice receiving only saline. Accordingly, SARS-CoV-2 spike S1 intoxication also increased the level of IL-6 in serum (FIG. 2J). However, intranasal treatment of wtAIDS peptide normalized body temperature (FIG. 2B), reduced lung neutrophil infiltration (FIG. 2C-F), decreased the level of IL-6 mRNA and protein as well as IL-1β mRNA in lungs (FIGS. 2G-1) and lowered the level of serum IL-6 in SARS-CoV-2 spike S1-intoxicated mice (FIG. 2J). These results were specific as mAIDS peptide had no such inhibitory effect (FIG. 2).

The wtAIDS peptide recovers heart functions and improves locomotor activities in SARS-CoV-2 spike S1-intoxicated mice: Many COVID-19 patients in the ICU develop cardiac arrhythmias[13]. Therefore, we examined if these cardiac features of COVID-19 could be modeled in SARS-CoV-2 spike S1-intoxicated mice. Different cardiac parameters are schematically presented in Supplementary FIG. 4. Spike S1-intoxication led to cardiac arrhythmias in mice as indicated by non-invasive ECG (FIG. 3A-B), an increase in heart rate (FIG. 3E), RR interval (FIG. 3F), JT interval (FIG. 3G), and R amplitude (FIG. 3H) and a decrease in heart rate variability (FIG. 3I), QRS interval (FIG. 3J) and QT interval (FIG. 3K). However, treatment with wtAIDS, but not mAIDS, peptide led to normalization of ECG (FIGS. 3A-D) and stabilization of heart rate (FIG. 3E), RR interval (FIG. 3F), JT interval (FIG. 3G), R amplitude (FIG. 3H), heart rate variability (FIG. 3I), QRS interval (FIG. 3J), and QT interval (FIG. 3K) in SARS-CoV-2 spike S1-intoxicated mice.

Next, to examine whether spike S1 intoxication also caused functional deficits, we monitored locomotor and open-field activities. Spike S1 insult decreased overall locomotor activities as evident by heat map (FIG. 5A), distance travelled (FIG. 5B), velocity (FIG. 5C), cumulative duration (FIG. 5D), and rotorod performance (FIG. 5E). Similar to normalization of heart functions, wtAIDS, but not mAIDS, peptide also improved SARS-CoV-2 spike S1-induced hypolocomotion (FIG. 5).

DISCUSSION

Until now, almost 900,000 people died throughout the world due to COVID-19. Therefore, untangling the mechanism of the disease process of COVID-19 and designing an effective therapeutic approach to slow down the disease and stop the death are of paramount importance. ACE2 being the main player of the classical renin-angiotensin pathway plays an important role in vascular diseases[3]. Since SARS-CoV-2 binds ACE2 and causes its internalization to enter into human cells, COVID-19 is particularly deleterious to patients with underlying cardiovascular issues. Although ACE2 inhibitors are available[14] and such inhibitors may stop the entry of SARS-CoV-2 into human cells, it is not possible to inhibit this beneficial molecule. Therefore, through structural analysis of the interaction between SARS-CoV-2 and ACE2, we have designed a small hexapeptide corresponding to the ACE2-interacting domain of SARS-CoV-2 (AIDS). Since the spike S1 of SARS-CoV-2 interacts with ACE2, wtAIDS peptide unsettled the association between ACE2 and SARS-CoV-2 spike S1.

Although it has been shown that a subgroup of patients with severe COVID-19 symptoms suffer from cytokine storm[15], underlying mechanism was not known. Marked induction of proinflammatory cytokines (IL-6 and IL-1p) in human A549 lung cells by SARS-CoV-2 spike S1 even at a very low dose suggests that this spike subunit may contribute to cytokine storm in COVID-19 patients. Consistent to the inhibition of association between ACE2 and SARS-CoV-2 spike S1, wtAIDS peptide inhibited the expression of IL-6 and IL-1β in SARS-CoV-2 spike S1-intoxicated A549 lung cells. In contrast, wtAIDS peptide did not inhibit the expression of proinflammatory cytokines induced by poly IC (viral double-stranded RNA mimic), Tat (transactivator of HIV-1 transcription) and flagellin (a component of bacterial infection), indicating the selective nature of wtAIDS peptide. Most importantly, the beauty of our finding is that wtAIDS peptide corresponds to peptide sequence of SARS-CoV-2. Therefore, it will only inhibit the binding of SARS-CoV-2 with ACE2 without affecting basal level and beneficial functions of ACE2. Moreover, it will function only in the presence of SARS-CoV-2.

Developing a small animal model system is an important step in understanding mechanisms associated to deadly cardiovascular and pulmonary issues of COVID-19 and evaluating effective drugs for this global pandemic. While handling live SARS-CoV-2 has many biosafety requirements, here, we describe the development of a very simple and live virus-free model of mimicking important cardiac and respiratory symptoms of COVID-19 in mice. SARS-CoV-2 spike S1 containing the RBD sequence is located at the N-terminus of the spike protein. Since most of the neutralizing epitopes are located within the spike S1, this spike subunit has become an important candidate for vaccine development. Interestingly, here, we demonstrated that intranasal administration of the same spike S1 was capable of inducing many key features of COVID-19 (fever, lung inflammation, lung neutrophil infiltration, increase in serum IL-6, and arrhythmias) in normal mice. Therefore, nasally SARS-CoV-2 spike S1-intoxicated mice could be used as a virus-free mouse model for testing different therapeutic options against COVID-19.

Until now, there is no effective therapy and also no approved vaccines for COVID-19. Although hydroxychloroquine showed some promise in the beginning, several clinical trials have ruled out the use of hydroxychloroquine in COVID-19[10]. Only, Remdesivir has been approved for emergency use in COVID-19[16]. Although s.c. injection of some ICU patients with IFN β-1b led to decrease in mortality rate[17], further randomized clinical trials with large sample size are needed for the exact estimation of survival benefit by this multiple sclerosis drug. Reduction of fever, protection of lungs, normalization of heart functions, and improvement in locomotor activities in SARS-CoV-2 spike S1-intoxicated mice by intranasal treatment with wtAIDS peptide suggest that selective targeting of SARS-CoV-2:ACE2 contact by wtAIDS peptide may be beneficial for COVID-19. The wtAIDS peptide should target only the SARS-CoV-2-dependent ACE2 pathway without inhibiting normal physiological functions of ACE2. Accordingly, in a group of control mice, we also did not notice any drug-related side effect (e.g. hair loss, appetite loss, weight loss, untoward infection and irritation, etc.) upon treatment with intranasal wtAIDS peptide. In summary, our preclinical studies have identified intranasal AIDS peptide as a primary or adjunct therapeutic option for COVID-19 patients.

Materials and Methods

Reagents

Human A549 lung carcinoma cell line (cat #CCL-185) and F-12K medium (cat #30-2004) were purchased from ATCC. Hank's balanced salt solution, 0.05% trypsin, and antibiotic-antimycotic were purchased from Mediatech (Washington, D.C.). Fetal bovine serum (FBS) was obtained from Atlas Biologicals. ACE2:SARS-CoV-2 Spike Inhibitor Screening Assay Kit (Cat #79936) was purchased from BPS Bioscience. Recombinant COVID-19 Spike protein S1 was purchased from MyBioSource (Cat #MBS553722) and Abeomics (Cat #MBS553722). Anti-SARS-CoV-2 Spike S1 antibody (Cat #A3000-50) was bought from BioVision. Human IL-1β ELISA and IL-6 ELISA kits were bought from ThermoFisher.

Animals and Intranasal Delivery of AIDS Peptides

Mice were maintained and experiments conducted in accordance with National Institute of Health guidelines and were approved by the Rush University Medical Center IACUC. C57/BL6 mice (6-8 week old; Envigo) of both sexes were treated intranasally with wtAIDS or mAIDS peptides (100 ng/mouse/d) for 7d. Briefly, AIDS peptides were dissolved in 2 μl normal saline, mice were hold in supine position and 1 μl volume was delivered into each nostril using a pipetman.

Typically, any animal experiment is justified with 99% confidence interval that generates p=0.99 and (1-p)=(1-0.99)= 0.01; ε is the margin of error=0.05. Based on these value, the resultant sample size is: N=

$$N = \frac{1,28^2 * 0.99(1-0.99)}{0.05^2} = \frac{1,28^2 * 0.99 * 0.01}{0.05^2} = \frac{0.016}{0.0025} = 6.48 \sim 6$$

Therefore, six mice (n=6) were used in each group.

Intoxication of C57/1BL6 Mice with Recombinant SARS-CoV-2 Spike S1

C57/1BL6 mice (6-8 week old; Envigo) of both sexes were intoxicated with recombinant SARS-CoV-2 spike S1 (50 ng/mouse/d) intranasally. Briefly, recombinant spike S1 was dissolved in 2 μl normal saline, mice were hold in supine position and 1 μl volume was delivered into each nostril using a pipetman. Control mice received only 2 μl saline.

Non-Invasive ECG Recording

Prior to ECG recording, mice were acclimatized to the ECG pulse transducer pad (AD instruments TN 012/ST, USA) and the experimental housing conditions. ECG pulse transducer pad was placed around the heart of each animal and ECG recording was carried out for 120s. For ECG analysis, electrocardiography data were exported from the Labchart pro, version 8.0 (Power Lab 4/35 model) as raw data format and the digital signal processing was performed using this software. The recording was conducted for 120 s and the ECG signals were recorded at a sampling range of 20 mV with 4 beats/s sampling rate as recommended in the software for mouse ECG analysis. The ECG tracing was visually reviewed for identifying possible arrythmias or other anomalous complexes. Prior to analyze the data, in the Labchart pro software ECG setting data source was kept for ECG channel selected as the channel 1 out of the multiple channels and selected for whole channel specific for mouse species. In the detection setting, typical QRS width was reserved at 10 ms and R wave kept at least 60 ms apart with the alignment maintained at QRS maximum. In the analysis portion, pre-baseline was kept at 10 ms with maximum at 50 ms. We selected for rodent waves and measured ST segment height at 10 ms height. All the ECG parameters including PQ interval, QRS interval, QT interval, T duration, JT interval as well as P Amplitude, Q amplitude, R Amplitude, S amplitude, T amplitude were calculated. The recording and analysis settings were kept same for all the experimental mice included in this study.

Monitoring Lung Infiltration and Pathology

After treatment, animals were anesthetized with ketamine/xylazine injectable followed by transcardial perfusion[18]. The lungs were collected and processed for histological studies. Hematoxylin-eosin (HE) (SigmaAldrich, St Louis, Mo.) staining was performed from 4 μm thick paraffin embedded sections and used for studying the general lung tissue morphology. Number of epithelial cells, and the number infiltrated neutrophils in alveolar spaces and interstitial space were analyzed by ImageJ. At least ten 40× fields from each group were chosen for the counting of the epithelial and infiltrated neutrophils.

In Silico Structural Analysis

In silico structural analysis was performed as described earlier[19,20]. Briefly, by utilizing the protein preparation tools from the Schrodinger, Inc. platform, we evaluated the quality of the crystal structure of human ACE2 and SARS-CoV-2 spike S1. After assessing the quality of the crystal structure, hydrogens were added to the hydrogen bond orientation, charges were added in the Optimized Potential for Liquid Simulations (OPLS3) force field followed by adding missing atoms and side chains of the different residues of both the proteins. Finally, the complex structure was subjected to energy minimization in OPLS3 force field to make it torsion free. After the protein predation, we extracted out the spike protein from the ACE2 and then applied the dynamic hydrogen bonding module in order to find potential hydrogen bonds between the two structures. After assessing the H-bonds, we also evaluated other interactions such as hydrophobic interactions between the two structures as shown in FIG. 1A.

ACE2:SARS-CoV-2 Spike Binding Assay

The effect of wtAIDS and mAIDS peptides on the binding of ACE2 and SARS-CoV-2 spike was examined using the ACE2:SARS-CoV-2 Spike inhibitor screening assay kit (BPS Bioscience, San Diego, Calif.) according to manufacturer's instructions. Briefly, 96-well nickel-treated plate provided by the manufacturer was coated with ACE2 solution. After washing with immuno buffer and incubation with blocking buffer, different concentrations of AIDS peptides were added to each well followed by addition of SARS-CoV-2 Spike (RBD)-Fc. After washing and incubation with blocking buffer, plates were treated with anti-mouse Fc-HRP followed by addition of an HRP substrate. Resultant chemiluminescence was measured using Perkin Elmer multimode microplate reader, Victor X5.

Semi-Quantitative RT-PCR Analysis

Total RNA was isolated from A549 lung cells and mouse lungs using RNAeasy Mini kit (Qiagen, Germantown, Md.) and Ultraspec-II RNA reagent (Biotecx Laboratories, Inc., Houston, Tex.), respectively. To remove any contaminating genomic DNA, total RNA was digested with DNase. RT-PCR was carried out as described earlier[21,22] using a RT-PCR kit (Clontech, Mountain View, Calif.). Amplified products were electrophoresed on a 1.8% agarose gels and visualized by ethidium bromide staining. Message for the GAPDH gene was used to ascertain that an equivalent amount of cDNA was synthesized from different samples.

Real-Time PCR Analysis

DNase-digested RNA was analyzed by real-time PCR in the ABI-Prism7700 sequence detection system (Applied Biosystems, Foster City, Calif.) as described earlier[21,22].

ELISA for IL-6

IL-6 ELISA was performed in lung homogenates as described earlier[23] using an assay kit (eBioscience) according to manufacturer's instruction.

Statistical Analysis

Statistical analyses were performed using Graphpad prism 8.0 (GraphPad Software, Inc., La Jolla, Calif.). Mouse behavioral measures were examined by an independent one-way ANOVA using SPSS. Homogeneity of variance between test groups was examined using Levene's test. Post-hoc analyses were conducted using Tukey's tests. Other data were expressed as means t SD of three independent experiments. Statistical differences between means were calculated by the Student's t-test (two-tailed). A p-value of less than 0.05 (p<0.05) was considered statistically significant.

Example 2

Angiotensin-converting enzyme 2 (ACE2) on host cells serves as the receptor for SARS-CoV-2, and therefore, for targeting COVID-19 from therapeutic angle, we designed a hexapeptide corresponding to the spike S1-Interacting Domain of ACE2 Receptor (SPIDAR) (FIGS. 9A-B) that inhibits the association between ACE2 and spike S1 of SARS-CoV-2 (FIG. 9C).

Wild type (wt) SPIDAR:$^{37}$ EDLFYQ$^{42}$ (SEQ ID NO:9)

Mutated (m) SPIDAR:$^{37}$ EKLFYG$^{42}$ (SEQ ID NO:10)

Positions of mutations are underlined.

Intranasal treatment with wtSPIDAR as described above, but not mSPIDAR, decreased the level of proinflammatory molecules in lungs and serum of a mouse model of COVID-19 (FIGS. 10A-E). The wtSPIDAR, but not mSPIDAR, also normalized serum level of C-reactive protein (CRP) and reduced fever (FIG. 10F-G). Moreover, wtSPIDAR, but not mSPIDAR, also attenuated infiltration of neutrophils into the lungs (FIGS. 11A-E), reduced arrhythmias (FIGS. 12A-J), and improved locomotor activities (FIG. 13) in a mouse model of COVID-19. Therefore, selective targeting of SARS-CoV-2 spike S1-to-ACE2 interaction by wtSPIDAR is beneficial for COVID-19 treatment.

Example 3

Studies will be conducted to determine the effects of different peptides that inhibited the binding between ACE2 and SARS-CoV-2 spike S1 using the protocols described in Example 1. By way of non-limiting example, studies will be conducted using peptides having at least 80% identity to SEQ ID NO: 3, SEQ ID NO: 4, SEQ ID NO: 5 and SEQ ID NO: 6.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

1 Ledford, H. How does COVID-19 kill? Uncertainty is hampering doctors' ability to choose treatments. *Nature* 580, 311-312, doi:10.1038/d41586-020-01056-7 (2020).
2 Machhi, J. et al. The Natural History, Pathobiology, and Clinical Manifestations of SARS-CoV-2 Infections. *J Neuroimmune Pharmacol* doi:10.1007/s11481-020-09944-5 (2020).
3 Zaman, M. A., Oparil, S. & Calhoun, D. A. Drugs targeting the renin-angiotensin-aldosterone system. *Nat Rev Drug Discov* 1, 621-636, doi:10.1038/nrd873 (2002).
4 Vickers, C. et al Hydrolysis of biological peptides by human angiotensin-converting enzyme-related carboxypeptidase. *J Biol Chem* 277, 14838-14843, doi:10.1074/jbc.M200581200 (2002).
5 Stower, H. Spread of SARS-CoV-2. *Nat Med* 26, 465, doi:10.1038/s41591-020-0850-3 (2020).
6 Du, L. et al. The spike protein of SARS-CoV-a target for vaccine and therapeutic development. *Nat Rev Microbiol* 7, 226-236, doi:10.1038/nrmicro2090 (2009).
7 Pia, L. Spatial resolution of SARS-CoV-2 lung infection. *Nat Rev Immunol* doi:10.1038/s41577-020-00432-8 (2020).
8 Edwards, M. R., Bartlett, N. W., Hussell, T., Openshaw, P. & Johnston, S. L. The microbiology of asthma. *Nat Rev Microbiol* 10, 459-471, doi:10.1038/nrmicro2801 (2012).
9 McCullers, J. A. The co-pathogenesis of influenza viruses with bacteria in the lung. *Nat Rev Microbiol* 12, 252-262, doi:10.1038/nrmicro3231 (2014).
10 Pahan, P. & Pahan, K. Smooth or Risky Revisit of an Old Malaria Drug for COVID-19? *J Neuroimmune Pharmacol* 15, 174-180, doi:10.1007/s11481-020-09923-w (2020).
11 Chand, S. et al. COVID-19-Associated Critical Illness-Report of the First 300 Patients Admitted to Intensive Care Units at a New York City Medical Center. *J Intensive Care Med* 35, 963-970, doi:10.1177/0885066620946692 (2020).
12 Costela-Ruiz, V. J., Illescas-Montes, R., Puerta-Puerta, J. M., Ruiz, C. & Melguizo-Rodriguez, L SARS-CoV-2 infection: The role of cytokines in COVID-19 disease. *Cytokine Growth Factor Rev;* doi:10.1016/j.cytogfr.2020.06.001 (2020).
13 Karamchandani, K., Quintili, A., Landis, T. & Bose, S. Cardiac Arrhythmias in Critically Ill Patients With COVID-19: A Brief Review. *J Cardiothorac Vasc Anesth*, doi:10.1053/j.jvca.2020.08.013 (2020).
14 Jiang, F. et al Angiotensin-converting enzyme 2 and angiotensin 1-7: novel therapeutic targets. *Nat Rev Cardiol* 11, 413-426, doi:10.1038/nrcardio.2014.59 (2014).
15 Mehta, P. et al. COVID-19: consider cytokine storm syndromes and immunosuppression. *Lancet* 395, 1033-1034, doi:10.1016/S0140-6736(20)30628-0 (2020).
16 Lamb, Y. N. Remdesivir. First Approval. *Drugs*, doi: 10.1007/s40265-020-01378-w (2020).
17 Rahmani, H. et al. Interferon beta-1b in treatment of severe COVID-19: A randomized clinical trial. *Int Immunopharmacol* 88, 106903, doi:10.1016/j.intimp.2020.106903 (2020).
18 Mondal, S., Jana, M., Dasarathi, S., Roy, A. & Pahan, K. Aspirin ameliorates experimental autoimmune encephalomyelitis through interleukin-11-mediated protection of regulatory T cells. *Sci Signal* 11, doi:10.1126/scisignal.aar8278 (2018).
19 Rangasamy, S. B. et al. Selective disruption of TLR2-MyD88 interaction inhibits inflammation and attenuates Alzheimer's pathology. *J Clin Invest* 128, 4297-4312, doi:10.1172/JCI96209 (2018).
20 Roy, A. et al HMG-CoA Reductase Inhibitors Bind to PPARalpha to Upregulate Neurotrophin Expression in the Brain and Improve Memory in Mice. *Cell Metab* 22, 253-265, doi:10.1016/j.cmet.2015.05.022 (2015).
21 Ghosh, A. et al. Selective inhibition of NF-kappaB activation prevents dopaminergic neuronal loss in a mouse model of Parkinson's disease. *Proc Natl Acad Sci USA* 104, 18754-18759 (2007).

22 Roy, A. et al Regulation of cyclic AMP response element binding and hippocampal plasticity-related genes by peroxisome proliferator-activated receptor alpha. *Cell Rep* 4, 724-737, doi:S2211-1247(13)00390-2 [pii]10.1016/j.celrep.2013.07.028 (2013).

23 Mondal, S. et al. IL-12 p40 monomer is different from other IL-12 family members to selectively inhibit IL-12Rbeta1 internalization and suppress EAE. *Proc Natl Acad Sci USA* 117, 21557-21567, doi:10.1073/pnas.2000653117 (2020).

The invention claimed is:

1. A composition comprising an isolated peptide that inhibits the association between SARS-CoV-2 spike S1 and Angiotensin Converting Enzyme-2 (ACE-2) without inhibiting the activity of ACE-2, wherein the isolated peptide consists of SEQ ID NO: 3, SEQ ID NO: 4, SEQ ID NO: 5, SEQ ID NO: 6, or SEQ ID NO: 7, or SEQ ID NO: 9.

2. The composition according to claim 1, wherein the peptide consists of SEQ ID NO: 5.

3. The composition according to claim 1, wherein the peptide consists of SEQ ID NO: 6.

4. The composition according to claim 1, wherein the peptide consists of SEQ ID NO: 7.

5. The composition according to claim 1, wherein the peptide consists of SEQ ID NO: 9.

6. The composition according to claim 1, wherein the peptide consists of SEQ ID NO: 3.

7. The composition according to claim 1, wherein the peptide consists of SEQ ID NO: 4.

8. The composition according to claim 1, comprising two or more isolated peptides selected from the group consisting of SEQ ID NO: 3, SEQ ID NO: 4, SEQ ID NO: 5, SEQ ID NO: 6, SEQ ID NO: 7 and SEQ ID NO: 9.

9. The composition according to claim 1, wherein the composition further comprises a cell penetrating peptide of SEQ ID NO: 13 joined to the N-terminus or the C-terminus of the isolated peptide.

10. A method of alleviating the symptoms associated with COVID-19, the method comprising administering a first agent to a subject in need thereof, the first agent comprising an isolated peptide that inhibits the association between SARS-CoV-2 spike S1 and Angiotensin Converting Enzyme-2 (ACE-2) without inhibiting the activity of ACE-2, wherein the isolated peptide is selected from the group consisting of SEQ ID NO: 3, SEQ ID NO: 4, SEQ ID NO: 5, SEQ ID NO: 6, SEQ ID NO:7, and SEQ ID NO: 9.

11. The method according to claim 10, wherein first agent comprises two or more peptides selected from the group consisting of SEQ ID NO: 3, SEQ ID NO: 4, SEQ ID NO: 5, SEQ ID NO: 6, SEQ ID NO: 7, and SEQ ID NO: 9.

12. The method according to claim 10, further comprising administering a second agent.

13. The method according to claim 10, wherein first agent is delivered nasally or by inhalation.

14. The method according to claim 12, wherein the second agent is delivered systemically.

15. A method of halting the further progression of or worsening of the symptoms associated with COVID-19, the method comprising administering a first agent to a subject in need thereof, the first agent comprising an isolated peptide that inhibits the association between SARS-CoV-2 spike S1 and Angiotensin Converting Enzyme-2 (ACE-2) without inhibiting the activity of ACE-2, wherein the isolated peptide is selected from the group consisting of SEQ ID NO: 3, SEQ ID NO: 4, SEQ ID NO: 5, SEQ ID NO: 6, SEQ ID NO: 7, and SEQ ID NO: 9.

16. The method according to claim 15, wherein the first agent comprises two or more peptides selected from the group consisting of SEQ ID NO: 3, SEQ ID NO: 4, SEQ ID NO: 5, SEQ ID NO: 6, SEQ ID NO: 7, and SEQ ID NO: 9.

17. The method according to claim 15, further comprising administering a second agent.

18. The method according to claim 15, wherein the first agent is delivered nasally or by inhalation.

19. The method according to claim 17, wherein the second agent is delivered systemically.

* * * * *